(12) United States Patent
Burr et al.

(10) Patent No.: US 6,202,259 B1
(45) Date of Patent: Mar. 20, 2001

(54) METHOD AND APPARATUS FOR DEPOSITING PARTICULATE MATERIAL IN A FIBROUS WEB

(75) Inventors: Randy Keith Burr, Neenah; John Wallace de Vos, Appleton; David Willis Heyn, Neenah; Richard Francis Keller, Fremont; Thomas George Olsen, Neenah, all of WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/455,029

(22) Filed: Dec. 3, 1999

(51) Int. Cl.[7] .................................................. D01G 13/00

(52) U.S. Cl. .................................. 19/145; 19/302; 19/304

(58) Field of Search ............................ 19/145, 145.5, 19/296, 297, 298, 299, 300, 301, 302, 303, 304; 264/113, 517, 518; 425/81.1

(56) References Cited

U.S. PATENT DOCUMENTS

| 2,624,079 | * | 1/1953 | Duvall ..................................... 19/302 |
| 4,666,647 | | 5/1987 | Enloe et al. . |
| 4,761,258 | | 8/1988 | Enloe . |
| 4,927,582 | | 5/1990 | Bryson . |
| 5,028,224 | * | 7/1991 | Pieper et al. ............................ 19/304 |
| 5,445,777 | * | 8/1995 | Noel et al. ........................... 425/81.1 |
| 5,628,090 | * | 5/1997 | Lock ...................................... 19/304 |

* cited by examiner

Primary Examiner—John J. Calvert
Assistant Examiner—Gary L. Welch
(74) Attorney, Agent, or Firm—Paul Yee

(57) ABSTRACT

A method and apparatus for depositing particulate material (30, 36) in an airlaid fibrous web (94) includes a moving of a forming surface (22) through a forming chamber (24), and a laying of a fibrous material (96) onto the forming surface to form the fibrous web. The particulate material is delivered into the forming chamber with an arcuate curved nozzle (86) which is positioned within the forming chamber at a location spaced from the forming surface.

25 Claims, 25 Drawing Sheets

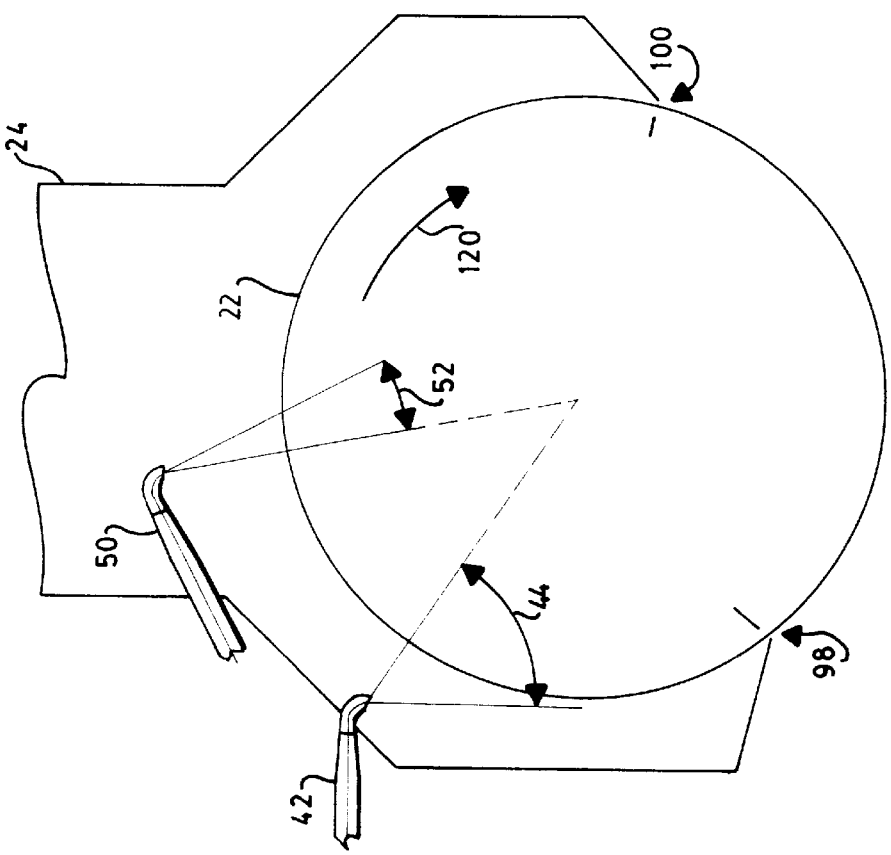
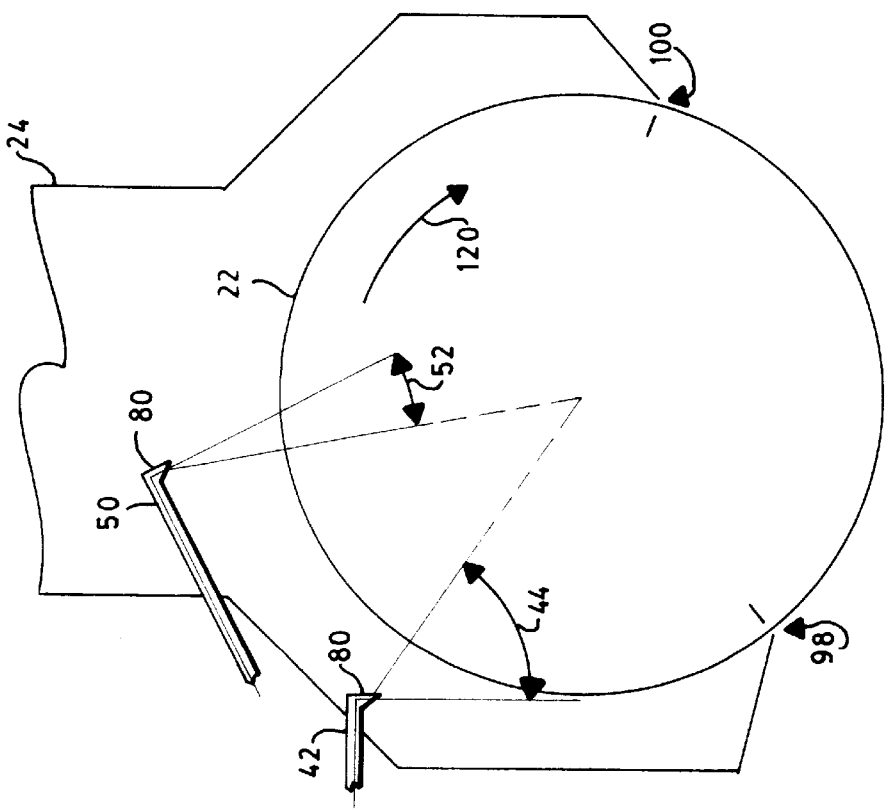

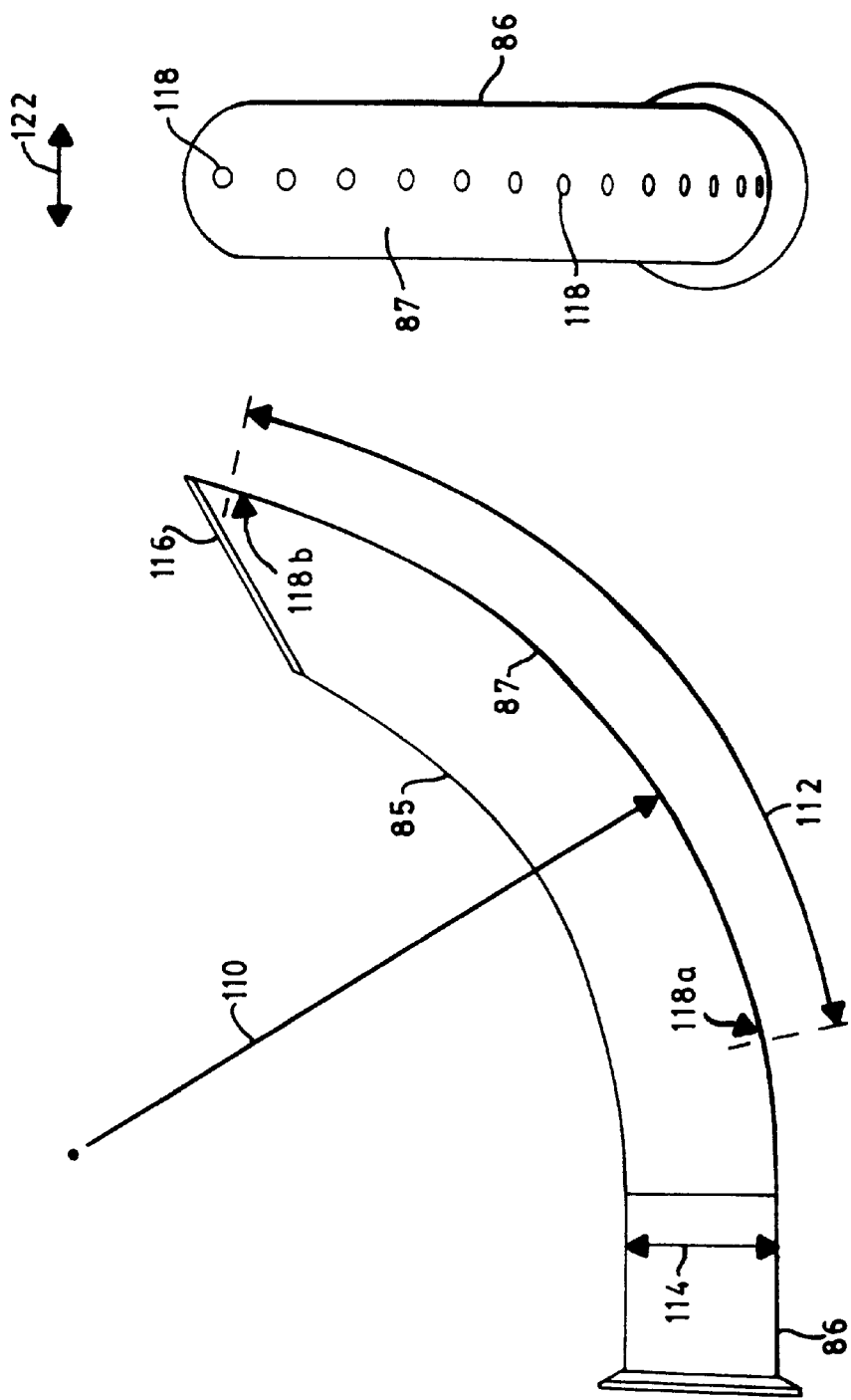

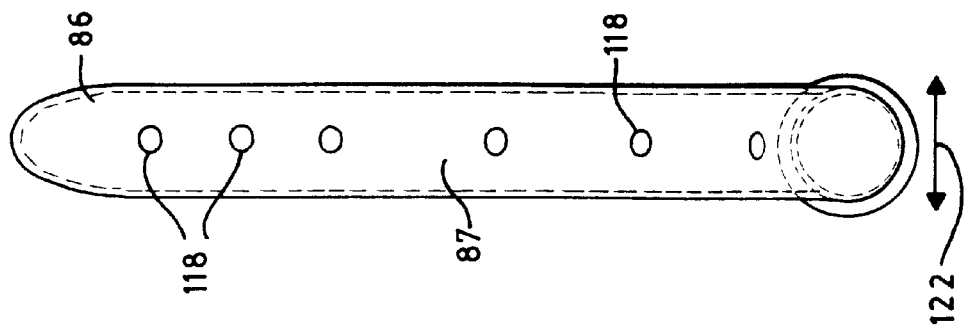
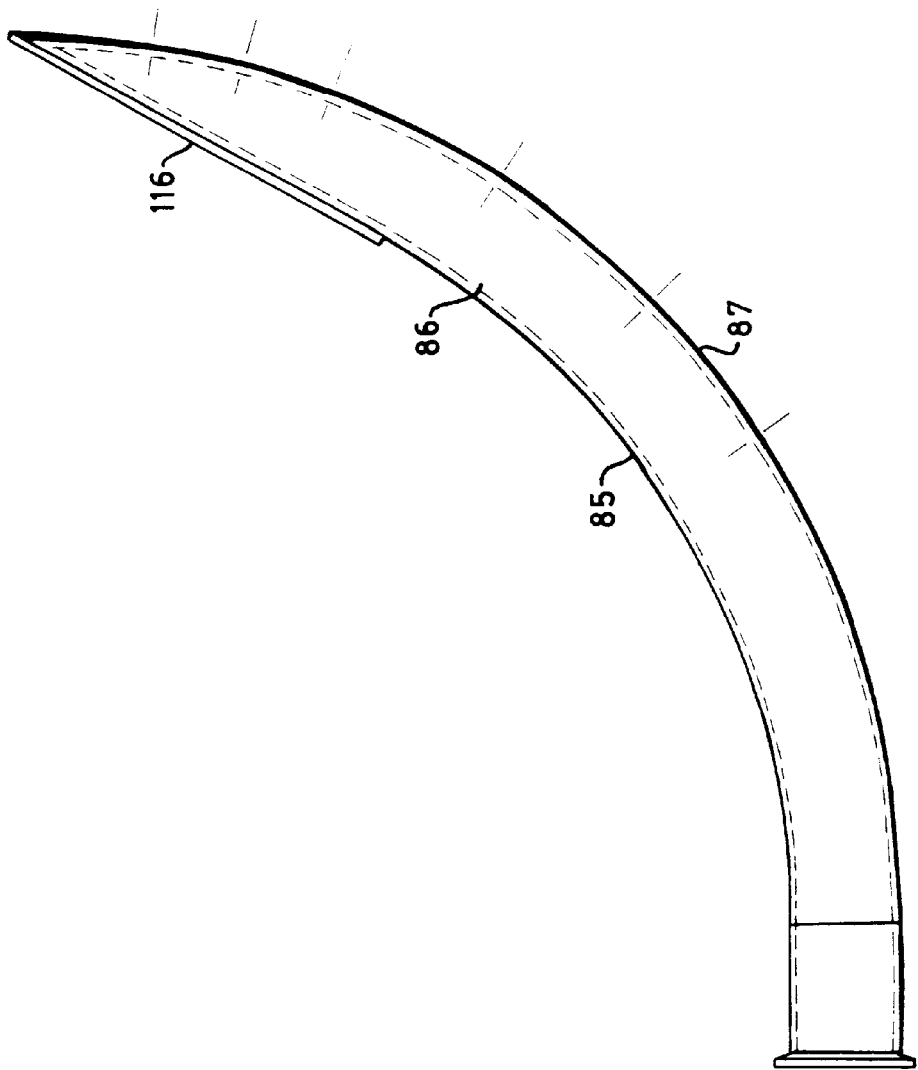

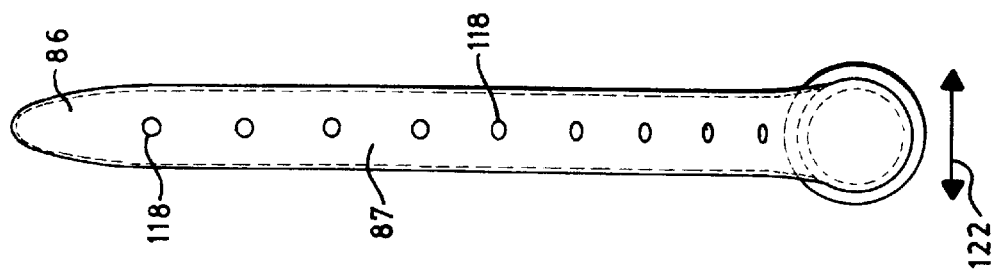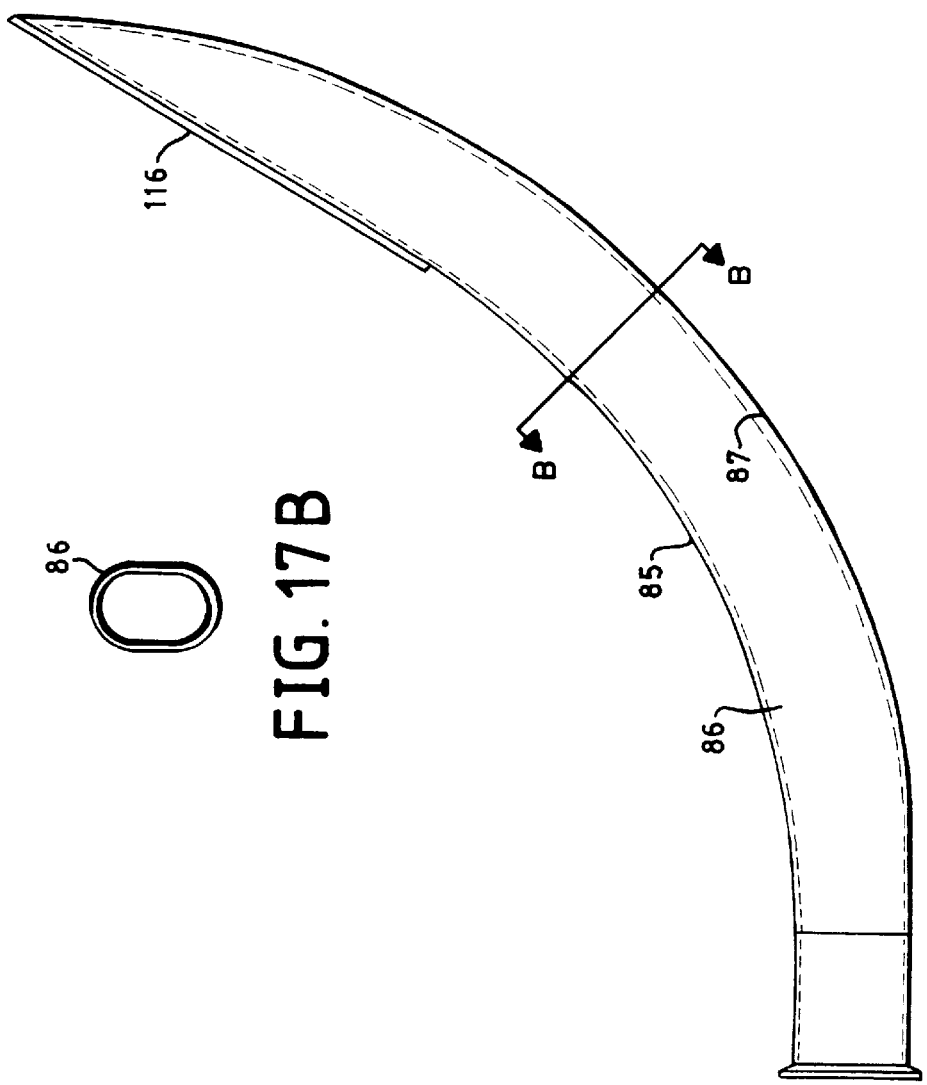

METHOD AND APPARATUS FOR DEPOSITING PARTICULATE MATERIAL IN A FIBROUS WEB

FIELD OF THE INVENTION

The present invention relates to a technique for producing an absorbent article. More particularly, the invention relates to a method and apparatus for depositing particulate material in a fibrous web.

BACKGROUND OF THE INVENTION

Absorbent articles and structures, such as absorbent pads and absorbent cores, have been formed by employing various techniques, such as wet forming techniques, and air laying techniques. Conventional air laying techniques have transported a foraminous forming surface, such as a forming screen, through a forming chamber. Fibrous materials and particulate materials have been introduced into the forming chamber, and a vacuum source has been employed to draw an air stream through the forming surface. The air stream entrains the fibers and particulate material for deposition onto the moving forming surface. In particular systems, a nozzle has been employed to deliver and direct the particulate material into the forming chamber, and the particles have been composed of superabsorbent material.

Multiple forming chambers have been employed to form different layers of material in a composite absorbent article. The different layers have included different types of particulate material, and have been composed of different types of fibrous material.

Such conventional techniques have been excessively complex and costly, especially those that employ multiple forming chambers. In addition, such conventional techniques have not adequately regulated the delivery of particles, such as superabsorbent particles, into desired locations within a fibrous web. More particularly, the conventional techniques have not adequately provided the deposition of particles into desired locations along a thickness dimension of the fibrous web. Also, the conventional delivery nozzles have not adequately provided the desired distributions and concentrations of the particulate material within the fibrous web. For example, the conventional delivery nozzles have not adequately generated desired, superabsorbent-rich strata within a selected absorbent article. As a result, there has been a continued need for improved techniques for controlling the deposition of particulate material in desired strata of a fibrous web, and for generating desired superabsorbent-containing strata within a composite absorbent article.

BRIEF DESCRIPTION OF THE INVENTION

The present invention provides a distinctive method and apparatus for depositing particulate material in an airlaid fibrous web. The technique includes a moving of a forming surface through a forming chamber, and a laying of the fibrous material onto the forming surface to form the fibrous web. In a particular aspect, the particulate material can be delivered into the forming chamber with an arcuate curved nozzle which is positioned within the forming chamber at a location spaced from the forming surface.

In its various aspects and configurations, the present invention can advantageously provide an effective and cost efficient technique for forming a desired distribution or concentration of particulate and fibrous material within an absorbent article. The technique of the invention can, for example, provide a desired distribution or concentration of superabsorbent material within a fibrous web, and can be configured to more effectively provide a predetermined location and distribution of superabsorbent material through the thickness of one or more selected fibrous strata of the desired absorbent article. In particular aspects, the technique of the invention better control the formation of selected strata having selected superabsorbent concentrations, and can better regulate desired separation distances between the strata along the thickness dimension of the article. As a result, the technique of the invention can better produce an absorbent article having improved absorbent performance, and can better produce an article having an improved combination of liquid uptake, liquid distribution, absorbent capacity, and leakage resistance.

BRIEF DESCRIPTION OF THE DRAWINGS

The present invention will be more fully understood and further advantages will become apparent when reference is made to the following detailed description of the invention and the drawings, in which:

FIG. 11A representatively shows a schematic side view of a forming system which incorporates first and second nozzles wherein at least one of the nozzles has a hooked shape generated with a deflector plate;

FIG. 11B representatively shows a schematic side view of a forming system which incorporates first and second nozzles wherein at least one of the nozzles has a hooked shape generated with an abruptly turned nozzle outlet section;

FIG. 13 representatively shows a schematic side view of a curved nozzle which can be employed with the present invention;

FIG. 13A representatively shows a schematic end view of the curved nozzle of FIG. 13;

FIG. 14A representatively shows a schematic end view of the curved nozzle of FIG. 14;

FIG. 15A representatively shows a schematic end view of the curved nozzle of FIG. 15;

FIG. 16A representatively shows a schematic end view of the curved nozzle of FIG. 16;

FIG. 16C representatively shows a schematic end view of the curved nozzle of FIG. 16B;

FIG. 17 representatively shows a schematic side view of a curved nozzle which includes an oval cross-sectional shape;

FIG. 17A representatively shows a schematic end view of the curved nozzle of FIG. 17;

FIG. 17B representatively shows a schematic cross-sectional view taken along line B-B of the curved nozzle of FIG. 17;

DETAILED DESCRIPTION OF THE INVENTION

The present invention can provide an improved method and apparatus for forming an article having a plurality of strata which include a fibrous material and a superabsorbent material. Desired arrangements of the invention can provide a selected configuration of the fiber and superabsorbent material in each stratum. In particular aspects, the invention can include a distinctive configuration of nozzles to form the desired strata. The invention can be employed to form absorbent structures employed in personal care products, such as infant diapers, feminine care products, children's training pants, adult incontinence products and the like.

It should also be noted that, when employed in the present disclosure, the terms "comprises", "comprising" and other derivatives from the root term "comprise" are intended to be open-ended terms that specify the presence of any stated features, elements, integers, steps, or components, but do not preclude the presence or addition of one or more other features, elements, integers, steps, components, or groups thereof.

Figure 1:
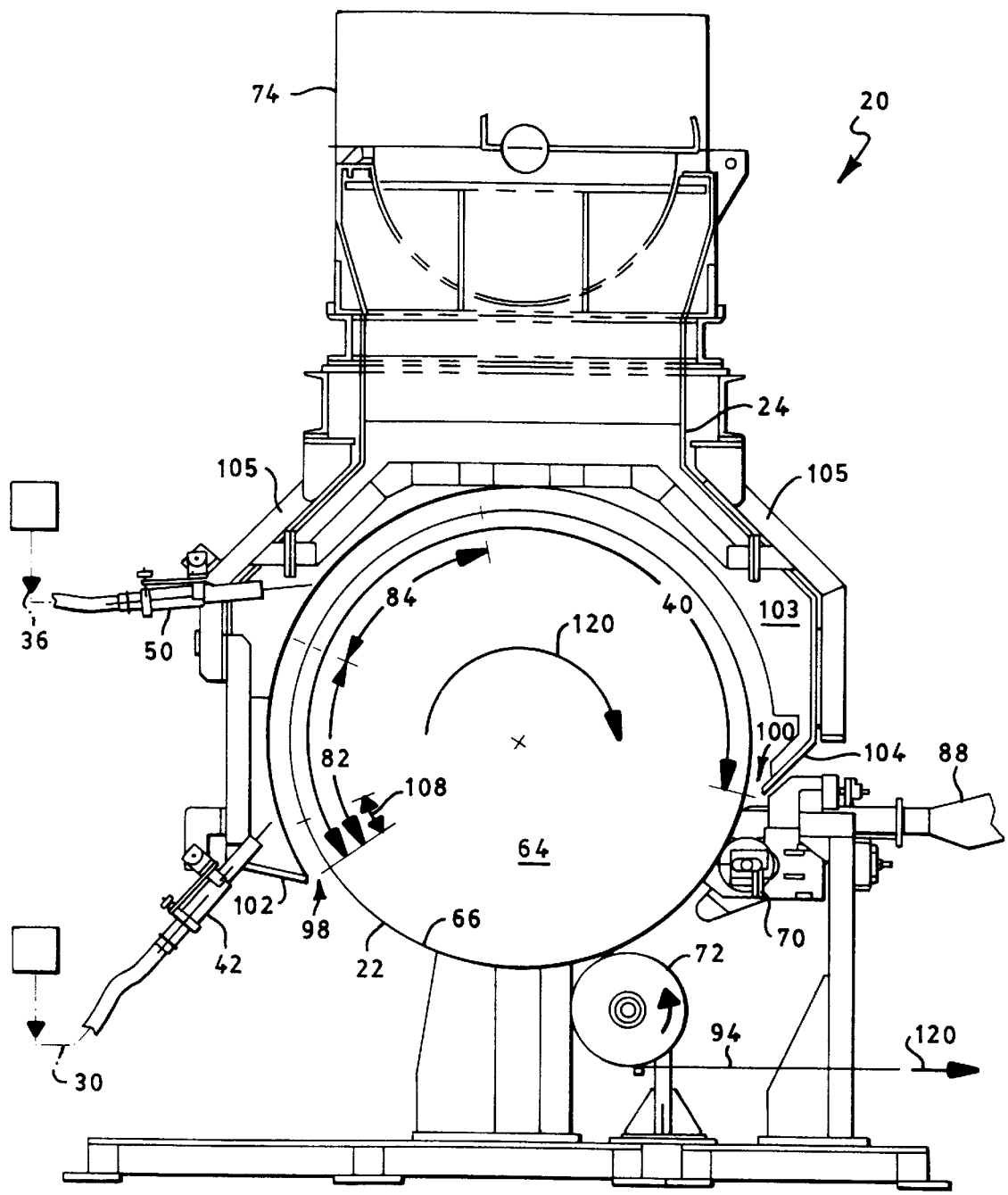
FIG. 1 representatively shows a schematic side view of a forming system of the invention which incorporates a rotatable forming drum.
Figure 2:
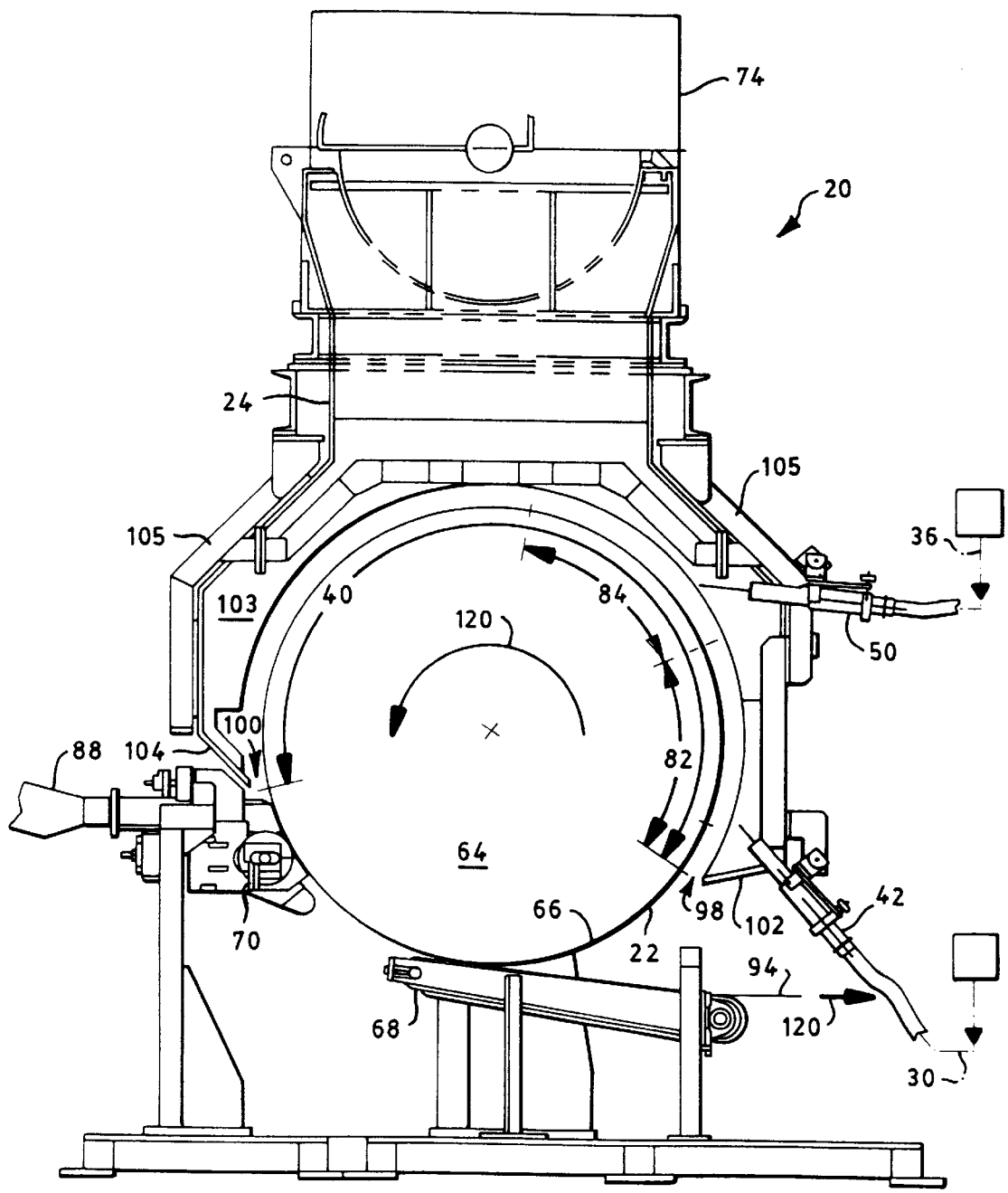
FIG. 2 representatively shows a schematic side view of an alternative configuration of a modified forming system which incorporates the rotatable forming drum.
Figure 13C:
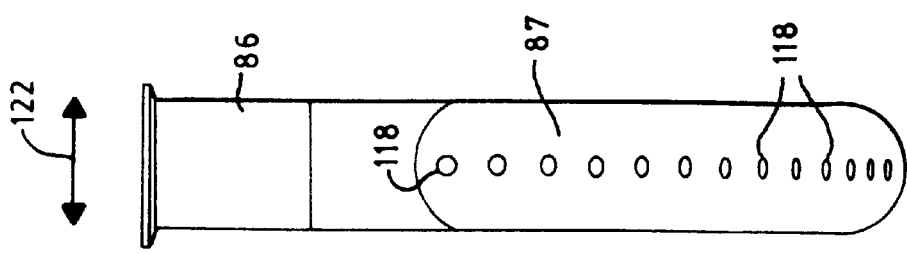
FIG. 13C representatively shows a schematic end view of the curved nozzle of FIG. 13B.

With reference to FIGS. 1 and 2, the process and apparatus 20 of the invention has an appointed machine-direction 120 and an appointed cross-direction 122 (e.g. FIG. 13A). For the purposes of the present disclosure, the machine-direction 120 is the direction along which a particular component or material is transported length-wise along and through a particular, local position of the apparatus and method. The cross-direction 122 lies generally within the plane of the material being transported through the process and is aligned perpendicular to the local machine-direction 120. Accordingly, in the view of the arrangement representatively shown in FIG. 1, the cross-direction 122 extends perpendicular to the plane of the sheet of the drawing.

Figure 11:
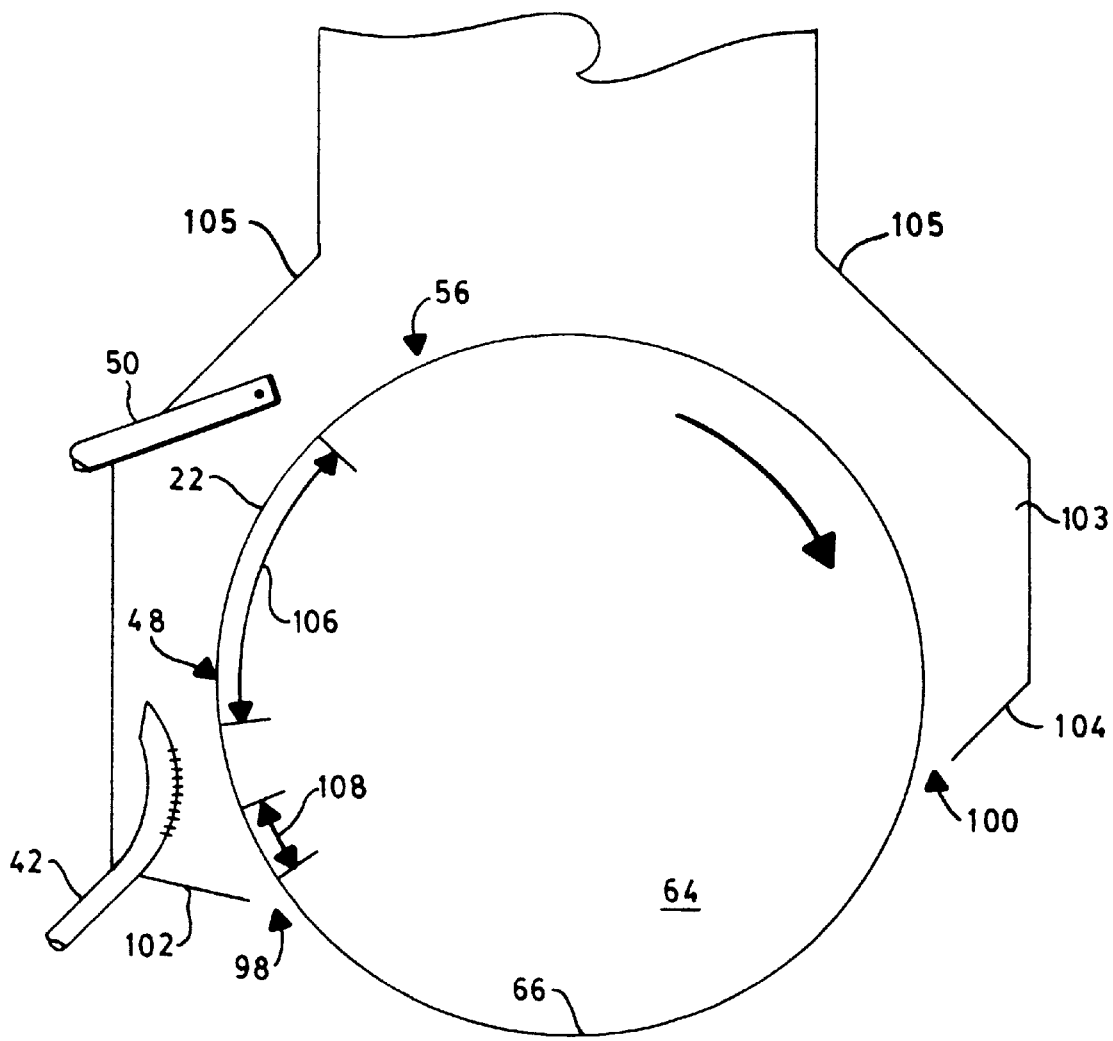
FIG. 11 representatively shows a schematic side view of a forming technique of the invention which incorporates an alternative nozzle system having first and second nozzles wherein at least one of the nozzles has a distinctively curved shape.
Figure 13B:
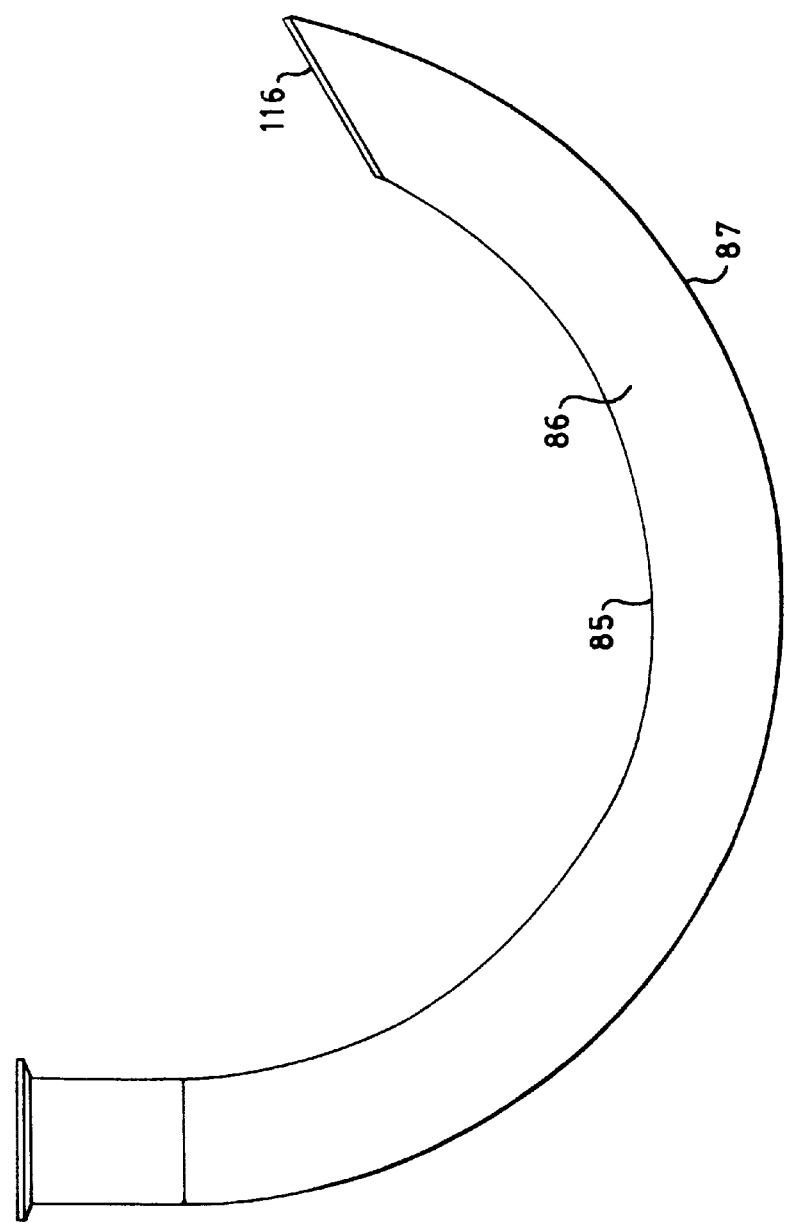
FIG. 13B representatively shows a schematic side view of alternative curved nozzle which has an increased arc length and extends along a greater arc angle.

With reference to FIGS. 11 and 13, the technique of the invention provides a distinctive method and apparatus for depositing particulate material, such as superabsorbent material, in an airlaid fibrous web 94. The technique includes a moving of a forming surface 22 through an operative forming chamber 24, and a laying of the fibrous material onto the forming surface to form the fibrous web. In a particular aspect, the particulate material can be delivered into the forming chamber with an arcuate curved nozzle 86 which is positioned within the forming chamber 24 at a location spaced from the forming surface 22.

In another aspects, the curved nozzle 86 can include an array of outlets 118 located in a radially outboard wall 87 of the curved nozzle. In still other aspects, the outlets can be generally aligned along a longitudinal dimension of said curved nozzle, and the outlets can have different sizes and shapes.

Figure 6:
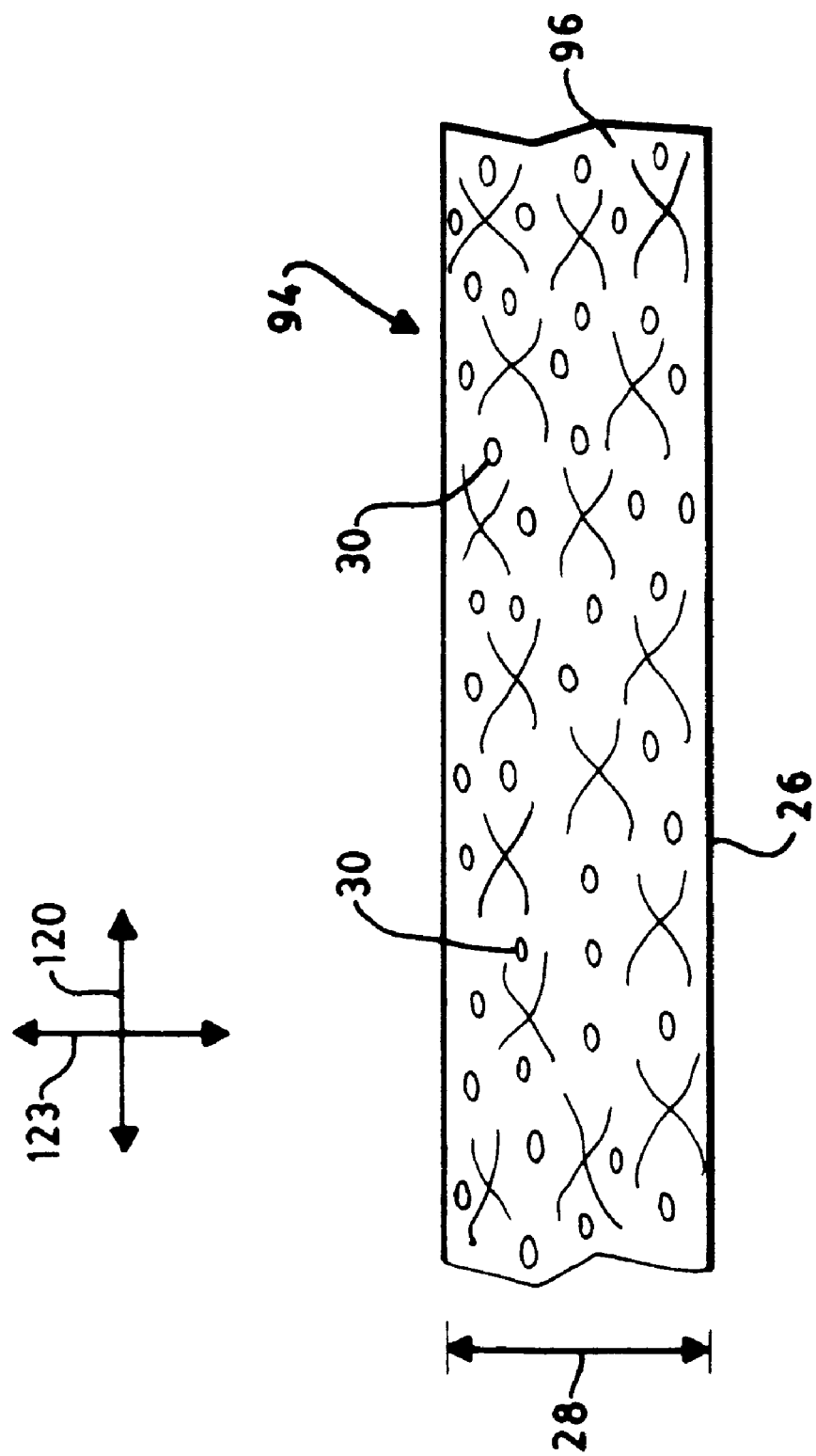
FIG. 6 representatively shows a schematic cross-sectional view of a web that can be produced with the forming system of FIG. 5, wherein the web has a substantially uniform distribution of superabsorbent particles in a matrix of fibers.

The method and apparatus of the invention can be employed to form an article, such as an article which includes the representatively shown absorbent web 94, and the article can have a plurality of strata which include superabsorbent material and fibrous material. Desirably, the fibrous material can provide an operative fibrous matrix for holding and containing the superabsorbent material, and the web has a z-directional, thickness dimension or direction 123 (e.g. FIG. 6).

A first fibrous stratum 26 of fiber material 96 (e.g. FIGS. 6 and 7) can be deposited onto the forming surface 22, and the first fibrous stratum 26 can have a first stratum thickness 28. In a particular aspect, a first quantity of superabsorbent material 30 can be directed to form a first superabsorbent-containing stratum or region which is in a selected combination with the first fibrous stratum 26. For example, the first quantity of superabsorbent material 30 can be directed to form a selected combination or arrangement with the fibers of the first fibrous stratum 26 to provide the first superabsorbent-containing stratum or region. In another aspect, a second fibrous stratum 32 of fibrous material can be deposited to overlie the first fibrous stratum 26, and the second fibrous stratum 32 can have a second stratum thickness 34. In a further aspect, a second quantity of superabsorbent material 36 can be directed to form a second superabsorbent-containing stratum or region which is in a selected combination with the second fibrous stratum 32. For example, the second quantity of superabsorbent material 36 can be directed to form a selected combination or arrangement with the fibers of the second fibrous stratum 32 to provide the second superabsorbent-containing stratum or region.

In particular configurations, the first quantity of superabsorbent material 30 may be operatively directed into the appointed first stratum thickness to combine with the first fiber material and form a first stratum or region having a fiber-superabsorbent mixture which is relatively rich in superabsorbent. Similarly, the second quantity of superabsorbent material 36 may be operatively directed into the appointed second stratum thickness to combine with the second fiber material and form a second stratum or region having a fiber-superabsorbent mixture which is relatively rich in superabsorbent. In desired configurations, the first superabsorbent material can have properties, such as physical and/or chemical characteristics, which differ from the properties of the second superabsorbent material. Optionally, the properties of the first and second superabsorbent materials can be substantially the same.

In the shown configurations, the technique of the invention can form a substantially continuous, fibrous web 94 which extends along the appointed machine-direction. Optionally, the technique may be configured to continually produce a segmented web, or a plurality of individually discrete and separate webs that are discontinuously or intermittently formed along the machine-direction. The web segments or individual webs may, for example, be positioned side-by-side along the cross-direction, positioned in series along the machine-direction, or positioned in combinations of such side-by-side and serial arrangements. The fibrous web is desirably composed of one or more materials that make the web absorbent to liquids, such as water, menses and/or urine.

Conventional air-forming systems have employed forming chambers to produce fibrous absorbent webs that contain particles of superabsorbent materials. Layered webs, with each web layer containing a selected amount or type of airlaid fiber and superabsorbent, have been produced by employing multiple forming chambers. Other layered webs have been produced by stacking individual layers after the layers have been previously formed. Such conventional techniques, however, have required excessive amounts of expensive equipment and excessive amounts of factory space. In addition, such conventional techniques have not adequately controlled the distributions and placements of the superabsorbent material through the thickness dimension of the overall, formed web, and have not sufficiently regulated the amounts and concentrations of the superabsorbent material at the desired placements. Where pre-formed layers are stacked to produce the final composite web, the interfaces between the stacked layers can excessively inhibit or otherwise degrade the desired transfer of liquid between the immediately adjacent layers.

In its various configurations and aspects, alone and in combination, the technique of the present invention can advantageously provide an improved method and apparatus for forming an article having a plurality of strata composed of superabsorbent material and fiber material in a selected matrix. In desired aspects, each of the formed strata can be individually distinct and can include a particular combination of selected fibers and selected superabsorbent. The technique of the invention can provide an efficient and cost effective technique for producing a desired distribution of two or more different types of superabsorbent material in a plurality of strata located along the thickness dimension of a composite absorbent article. The invention may, for example, avoid the need for multiple forming chambers, multiple fiberizers, and multiple forming drums or forming surfaces. As a result, the technique of the invention can be conducted with smaller amounts of expensive equipment, can be operated with lower energy costs, and can be more economically and efficiently conducted in less operating space. Additionally, the process and apparatus can be selectively adjusted to generate desired distributions and/or concentrations of the different superabsorbent materials within their corresponding, appointed strata. In particular, the process and apparatus can provide a desired amount and/or concentration of each selected type of superabsorbent material within its corresponding fiber material. The invention can also efficiently locate the superabsorbent material within its corresponding, appointed strata at desired positions along the thickness dimension of the formed web 94. Thus, the technique of the invention can advantageously produce a layered or stratified, composite web having a more intimate contact between the differing fibrous and/or superabsorbent materials of the immediately adjacent strata. Additionally, the technique can be configured to produce a desired blending or other graduated transition between the various materials of the adjacent strata. As a result, the technique of the invention can help produce a composite web having an improved flow and transfer of a selected liquid through the web thickness and between the individually configured strata.

With reference to FIGS. 1 and 2, the method and apparatus 20 for forming an article 94 includes a moving of a forming surface 22 through an operative forming chamber 24 along an selected forming path length 40. A first fibrous stratum 26 of fiber material 96 can be deposited onto the forming surface 22, and the first fibrous stratum 26 can have a first stratum thickness 28. A first quantity of a first superabsorbent material 30 can be distributed or otherwise directed to form a selected combination with the first fibrous material to provide a first superabsorbent-containing stratum. A second fibrous stratum 32 of fibrous material can be deposited to overlie the first fibrous stratum 26, and the second fibrous stratum 32 can have a second stratum thickness 34. A second superabsorbent material 36 can be distributed or otherwise directed to form a selected combination with the second fibrous material to provide a second superabsorbent-containing stratum.

As representatively shown, the method and apparatus of the invention can include a rotatable, vacuum forming drum 64 which is operatively enclosed by the forming chamber 24. The forming drum can have a circumferential, outer periphery 66 which provides the forming surface 22, and the moving of the forming surface can be provided by the rotation of the forming drum. A conventional source of a selected fibrous material, such as a supply reservoir or a conventional fiberizer 74, can be configured to provide an operative supply of fiber material into the forming chamber 24. As representatively shown, the fiberizer 74 can be operatively positioned above the forming chamber and can include a conventional, rotary hammermill, or the like. In alternative arrangements, the fiberizer may be located to the side of the forming chamber, or may be positioned at a selected remote location that is spaced away from the forming chamber.

The fiber material may include natural fibers, synthetic fibers, and combinations thereof. Examples of natural fibers can include wood pulp fibers, cotton fibers, wool fibers, silk fibers and the like, as well as combinations thereof. Synthetic fibers can include rayon fibers, polyolefin fibers, polyester fibers and the like, as well as combinations thereof. Typically, the fiber material includes wood pulp cellulose fibers.

With reference to FIGS. 1 and 2, an operative portion of the representatively shown forming drum 64 is appropriately enclosed by the forming chamber 24. The forming drum has an axis of rotation, and the direction of rotation can be either clockwise or counterclockwise, as desired. The configuration representatively shown in FIG. 1 has a substantially clockwise direction of rotation, and the configuration representatively shown in FIG. 2 has a substantially counter-clockwise direction of rotation. The selected forming drum 64 can be constructed and configured with a conventional "vacuum" system which generates a primary, air stream airflow from the interior of the forming chamber 24, through the forming surface 22 and into the interior of the forming drum 64. Examples of suitable forming drum systems for producing airlaid fibrous webs are well known. For example, see U.S. Pat. No. 4,666,647 entitled APPARATUS AND METHOD FOR FORMING A LAID FIBROUS WEB by K. Enloe et al. which issued May 19, 1987; U.S. Pat. No. 4,761,258 entitled CONTROLLED FORMATION OF LIGHT AND HEAVY FLUFF ZONES by K. Enloe which issued Aug. 2, 1988; the entire disclosures of which are incorporated herein by reference in a manner that is consistent herewith. Examples of techniques which can inject a directed stream of superabsorbent particles into a forming chamber are described in U.S. Pat. No. 4,927,582 entitled METHOD AND APPARATUS FOR CREATING A GRADUATED DISTRIBUTION OF GRANULE MATERIALS IN A FIBER MAT by R. E. Bryson which issued May 22, 1990; the entire disclosure of which is incorporated herein by reference in a manner that is consistent herewith.

The forming chamber 24 typically includes a front entrance wall 102, a rear exit wall 104, an appropriate pair of opposed side walls 103 (one of which is not shown), and a top cover wall 105, which are assembled together and configured in a conventional manner to suitably enclose an operative internal, forming volume of the forming chamber 24. As the forming drum 64 rotates, the fiber material is entrained by the air stream of the primary airflow drawn through the forming surface 22, and the fibers becomes deposited onto the forming surface. The fiber material is gradually accumulated onto the outer peripheral, forming surface 22 as the rotating forming drum moves the forming surface through the forming chamber. During the movement of the forming surface, the rate of the fiber accumulation and amount of fibrous web formation will vary, depending upon the process position along the length of the forming chamber. The greater rates of fiber accumulation and the greater amounts of web formation will typically occur towards the beginning, entrance-wall end of the forming chamber. Relatively smaller rates of fiber accumulation and relatively smaller amounts of web formation will typically occur towards the ending, exit-wall end of the forming chamber. After leaving the airlaying operation of the forming chamber, the formed web 94 can be subjected to further processing and assembly operations. For example, the web may be debulked and densified, and the web may be assembled with other desired components to form a final, finished article.

The forming surface 22 is typically a foraminous, air permeable component, such as provided by a wire forming cloth, a screen, a perforated plate or the like, as well as combinations thereof. Additionally, the air permeable component may be composed of metal, plastic, ceramic or the like, as well as combinations thereof. The forming surface may also include a porous tissue, a woven fabric, a nonwoven fabric and the like, as well as combinations thereof. The illustrated configuration can, for example, include a forming surface provided by a perforated plate, a hard-wire foraminous forming screen or the like. The forming surface can be composed of any durable material, such as durable plastic, metal or the like. For example, the forming surface may be composed of bronze or stainless steel.

With reference to FIGS. 1 and 2, the forming path length 40 is the length along the forming surface 22 which is bounded by the forming chamber 24. The forming path length 40 begins at a forming chamber entrance 98 and extends along the forming surface 22 to end at a forming chamber exit 100. In the representatively shown arrangements, the length 40 of the forming path extends circumferentially along the periphery 66 of the forming drum 64, and substantially corresponds to the circumferential length of the forming screen that is bounded by the forming chamber at any particular instant of time. Accordingly, the forming path length 40 can typically be the circumferential distance between the forming chamber entrance 98 and the forming chamber exit 100. Where the forming system optionally incorporates a flat, endless belt, forming surface, the forming path length typically begins at the forming chamber entrance and extends in a substantially straight line along the forming surface to end at the forming chamber exit (e.g. FIG. 3B).

With a beginning reference at the forming chamber entrance 98, the first nozzle 42 can be located to direct its corresponding superabsorbent material onto a portion of the forming surface 22 which becomes located within a first section 82 of the forming path length 40. Additionally, the second nozzle 50 can be located to direct its corresponding superabsorbent material onto a portion of the forming surface 22 which becomes located along a second section 84 of the forming path length.

In particular aspects, the first nozzle 42 can be positioned and aligned to direct and deposit its corresponding first quantity of superabsorbent material onto the portion of the forming surface which is located along a first section 82 of the forming path and substantially corresponds to a first 25% of the forming path length, as determined by employing the forming chamber entrance 98 as the starting point of the forming path length. In another aspect, a selected nozzle, such as the second nozzle 50, can be located and aligned to direct and deposit its corresponding second quantity of superabsorbent material onto the portion of the forming surface 22 which is located along a second section 84 of the forming path and substantially corresponds to a second 25% of the forming path length.

The desired aspects and configurations of the invention can advantageously improve the efficiency and effective of the forming process by directing the selected quantities of superabsorbent material toward portions of the forming path along which greater amounts fiber accumulation occur. Approximately 80%–90% of the web thickness can be generated within the first 50% of the forming path length. In addition, these aspects and configurations of the invention can allow an effective scarfing of the formed absorbent web without an excessive scrubbing and removing of superabsorbent material from the formed web.

In a desired configuration, for example, the forming path length 40 can extend along a distance which is approximately two-thirds of the outer circumference of the forming drum 64 and corresponds to a drum angle of about 240 degrees. Accordingly, the first 25% of the forming path length may correspond to approximately the first 60 degrees of the drum angle, as determined by employing the forming chamber entrance 98 as the starting point of the drum angle measurement. The second 25% of the forming path length may then correspond to approximately the second 60 degrees of the drum angle.

To provide the desired depositions and distributions of the selected quantities of superabsorbent material at the selected regions of the forming surface 22 and into the selected portions of the airformed web 94, the various of arrangements of the invention are configured to control and adjust important parameters. Such parameters include, but are not limited to, the movement speed of the forming surface, the inset distance between the entrance of the forming chamber and the first nozzle within the forming chamber, the offset distance between the nozzles inside the forming chamber, the alignment angle of each nozzle, the height distance between each nozzle and its corresponding local portion of the forming surface, the delivery speed of the material ejected from each nozzle, the lengthwise shaping of each nozzle, and the cross-sectional shaping of each nozzle, as well as combinations thereof.

In a particular arrangement of the invention, a first nozzle mechanism 42 may be mounted to a suitable support, such as the front entrance wall 102, and the first nozzle mechanism can be configured to direct and regulate a flow of the first quantity or quantities of superabsorbent material 30 into the forming chamber 24. The first nozzle is desirably positioned, oriented and aligned to direct the first superabsorbent material 30 onto an appointed first section 82 of the forming path length. As representatively shown, constantly changing portions or sections of the rotating forming drum 64 follow one another in sequence to become positioned along the first section of the forming path length during the turning movement of the forming drum.

The directing of the first superabsorbent material by the first nozzle 42 can operatively combine the first quantity or quantities of superabsorbent material with the fibrous material being deposited onto the forming surface 22 along the first section 82 of the forming path length. As a result, the fiber material can provide the first fibrous stratum 26, and the first superabsorbent material 30 can be operatively mixed or otherwise combined with the appointed fibrous material in the first fibrous stratum 26.

In the representatively shown configuration, a second nozzle 50 can be mounted to a suitable support, such as the cover wall 105, and can be configured to direct and regulate a flow of the appointed second quantity or quantities of superabsorbent material 36 into the forming chamber 24. The second nozzle is desirably oriented and aligned to direct the second quantity of superabsorbent material 36 onto an appointed second section 84 of the forming path length 40. After passing the first section 82 of the forming path, the constantly changing portions or sections of the moving forming drum 64 follow one another in sequence to become positioned along the second section 84 of the forming path length during the ongoing rotation of the forming drum.

The directing of the second superabsorbent material by the second nozzle 50 can operatively combine the second quantity or quantities of superabsorbent material with the fibrous material being deposited onto the forming surface 22 in the second section 84 of the forming path length. As a result, the fiber material can provide the second fibrous stratum 32, and the second superabsorbent material 36 can be operatively mixed or otherwise combined with the appointed fibrous material in the second fibrous stratum 32.

Where the forming drum 64 is employed, the drum can, for example, have a drum diameter of about 152 cm (about 5 ft). It should be readily appreciated, however, that other drums with larger or smaller diameters may optionally be employed, as desired.

In a particular aspect of the invention, the moving of the forming surface 22 can operatively translate the forming surface at a surface speed which is at least a minimum of about 100 m/min. The surface speed can alternatively be at least about 200 m/min, and optionally, can be at least about 350 m/min to provide improved performance. In other aspects, the surface speed can be up to a maximum of about 1000 m/min, or more. The surface speed can alternatively be not more than about 700 m/min, and optionally, can be not more than about 600 m/min to provide improved effectiveness.

The location of each nozzle along the selected forming path within the forming chamber can be identified in terms of a corresponding path-position value (PPV). For the purposes of the present disclosure the path-position value of each selected nozzle can be determined by the following formula:

$$PPV (\%) = 100 * Ln/Lp;$$

where: PPV=path-position value (as expressed in percent);
Ln=distance between the selected nozzle and the entrance of the forming chamber;
Lp=total length of the forming path provided by the forming chamber.

Accordingly, the location of each nozzle 42 and 50 along the length of the forming path of the fibrous web 94 within the forming chamber 24 can be defined by the path-position value of that nozzle.

In particular aspects of the invention, the first nozzle 42 can have a PPV which is at least a minimum of about 3%. The PPV of the first nozzle can alternatively be at least about 5%, and optionally, can be at least about 7% to provide improved performance. In other aspects, the PPV of the first nozzle can be not more than a maximum of about 30%. The PPV of the first nozzle can alternatively be not more than about 20%, and optionally, can be not more than about 12% to provide improved effectiveness.

In further aspects of the invention, the second nozzle 50 can have a PPV which is at least a minimum of about 20%. The PPV of the second nozzle can alternatively be at least about 24%, and optionally, can be at least about 26% to provide improved performance. In other aspects, the PPV of the second nozzle can be not more than a maximum of about 63%. The PPV of the second nozzle can alternatively be not more than about 50%, and optionally, can be not more than about 37% to provide improved effectiveness.

If the PPV of a selected nozzle is too low or too high, it can be excessively difficult to accurately control and direct the superabsorbent material to a desired location within the thickness of a selected fibrous stratum. In addition, the deposited superabsorbent material will not be adequately concentrated within its appointed fibrous stratum.

The first nozzle 42 and the second nozzle 50 are desirably spaced from each other along the movement direction of the forming surface 22. In the representatively shown configuration, for example, the nozzles are spaced along the circumferential direction of the forming drum 64. Additionally, the first and/or second nozzles can be selectively oriented and aligned to direct the first and second superabsorbent materials at appointed, discrete segments of the forming path length. The corresponding first and second segments of the forming path length can be offset along the machine-direction of the process, and can be distally spaced apart from each other along the circumferential dimension of the forming drum 64, or may be positioned substantially immediately adjacent to each other along the circumferential dimension of the drum. As representatively shown, the position, orientation or alignment of a particular nozzle is desirably determined with respect to the location and delivery direction of the outlet opening of the nozzle.

In particular aspects, the nozzle offset distance 106 (e.g. FIG. 7) between the adjacent nozzles along the forming path can be at least about 15.2 cm (about 6 inch). The nozzle offset distance can alternatively be at least about 30.5 cm (about 12 inch), and optionally, can be at least about 61 cm (about 24 inch) to provided improved performance. In other aspects, the nozzle offset distance can be not more than a maximum of about 200 cm. The nozzle offset distance can alternatively be not more than about 150 cm, and optionally, can be not more than about 100 cm to provide improved effectiveness.

In other aspects the nozzle offset distance 106 can be at least about 5% of the forming path length 40. The nozzle offset distance can alternatively be at least about 10%, and optionally, can be at least about 19% of the forming path length to provide improved performance. In other aspects, the nozzle offset distance can be not more than a maximum of about 63% of the forming path length. The nozzle offset distance can alternatively be not more than about 47%, and optionally, can be not more than about 31% of the forming path length to provide improved effectiveness.

Figure 8:
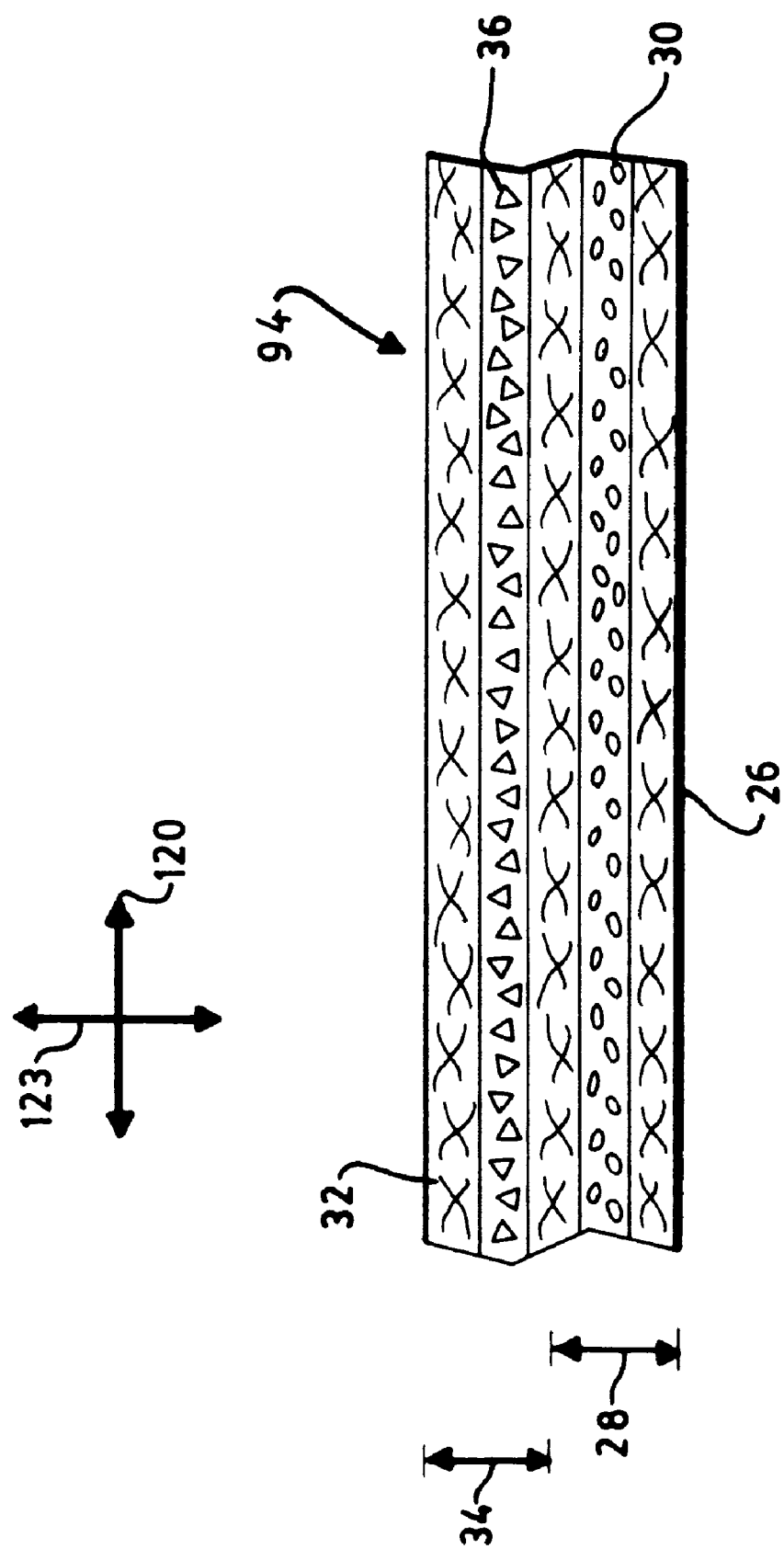
FIG. 8 representatively shows a schematic cross-sectional view of a web that can be produced with the forming system of FIG. 7.
Figure 9:
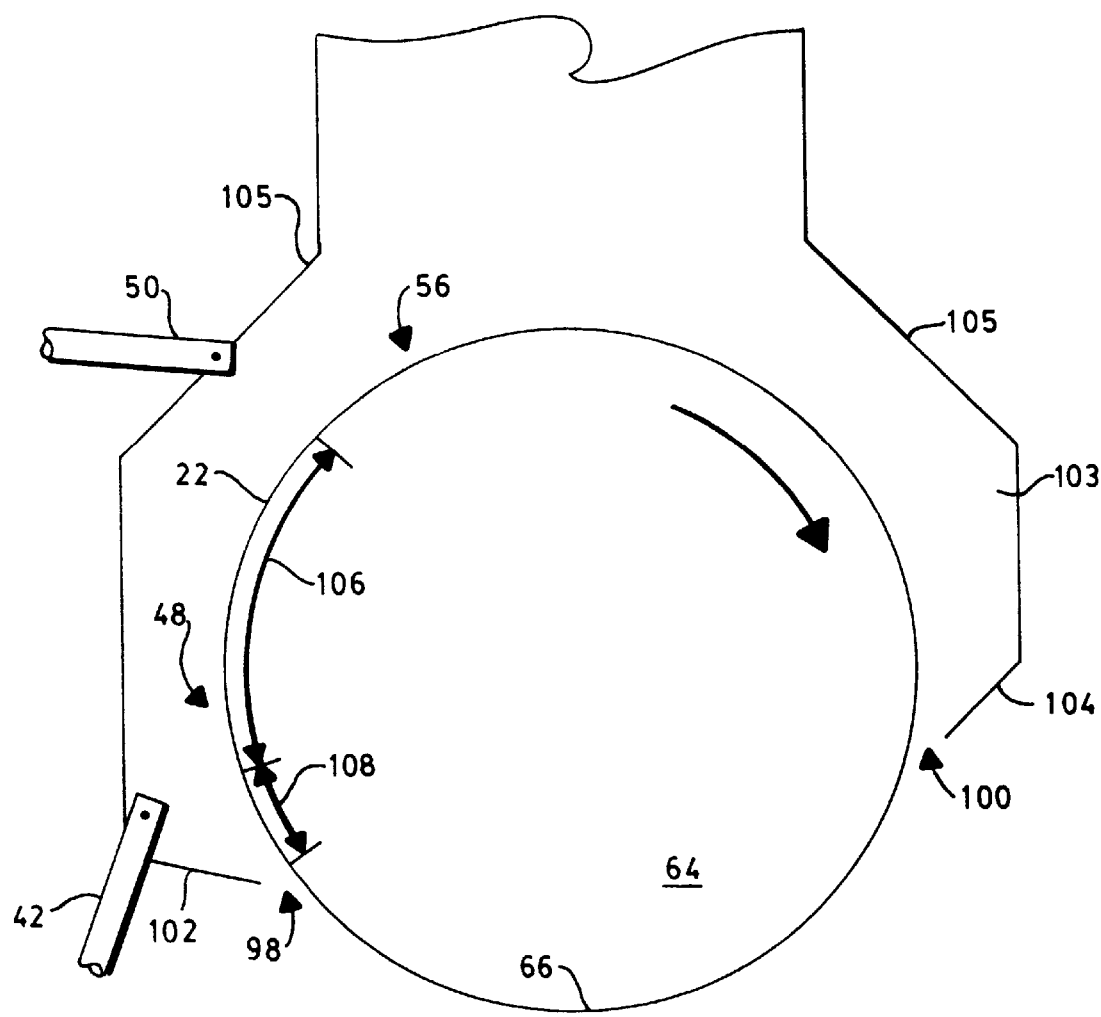
FIG. 9 representatively shows a schematic side view of a forming technique of the invention which incorporates another nozzle system having first and second nozzles.
Figure 12:
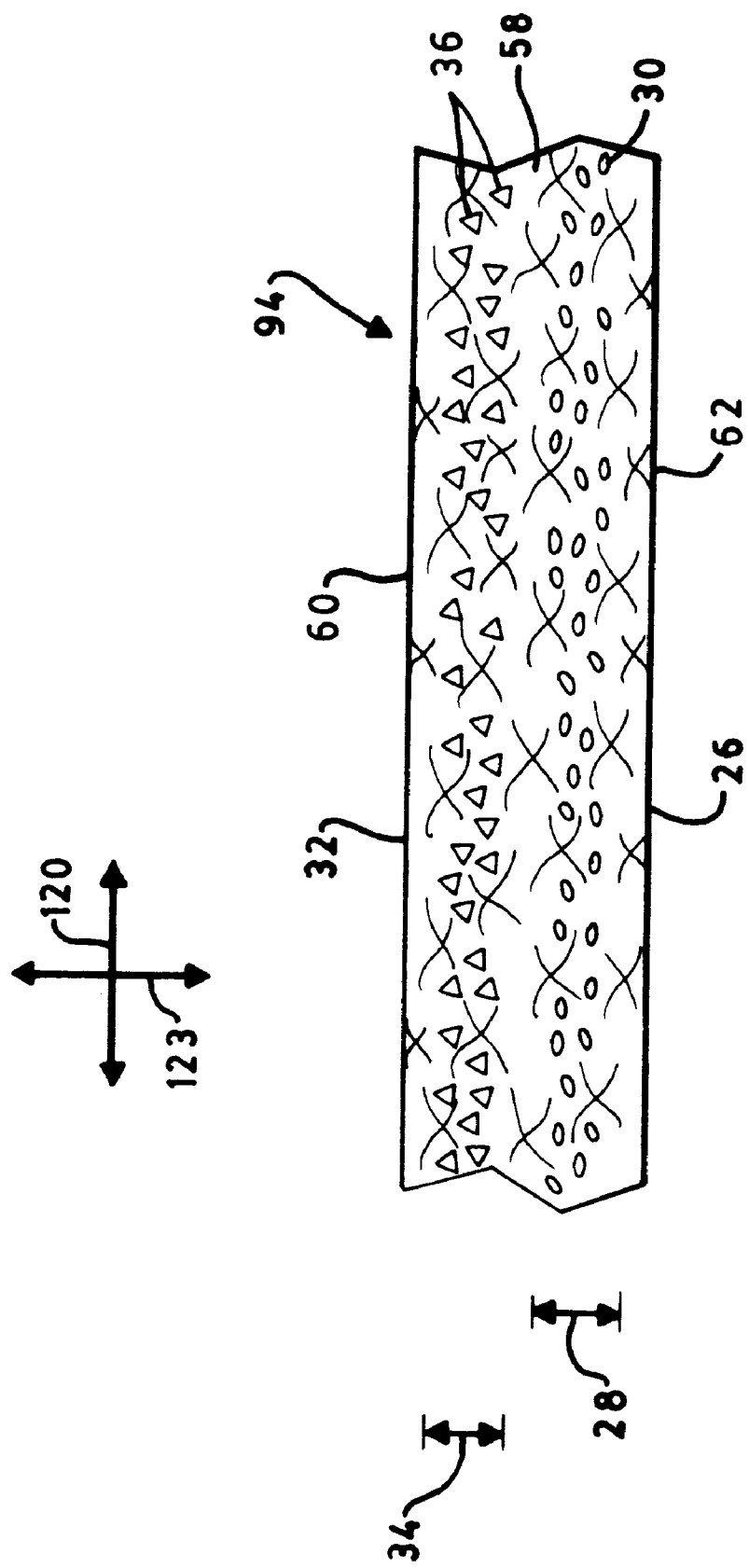
FIG. 12 representatively shows a schematic cross-sectional view of a web that can be produced with the forming system of FIG. 11.

If the offset distance 106 is too small, there can be an excessive overlapping or intermixing of the first and second quantities of superabsorbent materials. If the offset distance 106 is too large, there may be an excessive separation distance or an excessive amount fibrous material between the first and second quantities of superabsorbent materials. Additionally, the second quantity of the superabsorbent 36 may be positioned too close to the surface of the formed web 94 and the superabsorbent material may be exposed and subjected to excessive scarfing and removal by the scarfing roll 70.

Where the first nozzle 42 and the second nozzle 50 are operatively configured to direct and concentrate their corresponding superabsorbent materials onto separate, spaced apart segments of the forming path length, the technique of the invention can advantageously generate a third fibrous stratum 58 which is interposed between the first fibrous stratum 26 and the second fibrous stratum 32, as representatively shown in FIG. 8 and 12. The third fibrous stratum 58 can contain a relatively lower amount of superabsorbent material, as compared to the first fibrous stratum 26 and the second fibrous stratum 32.

Figure 10:
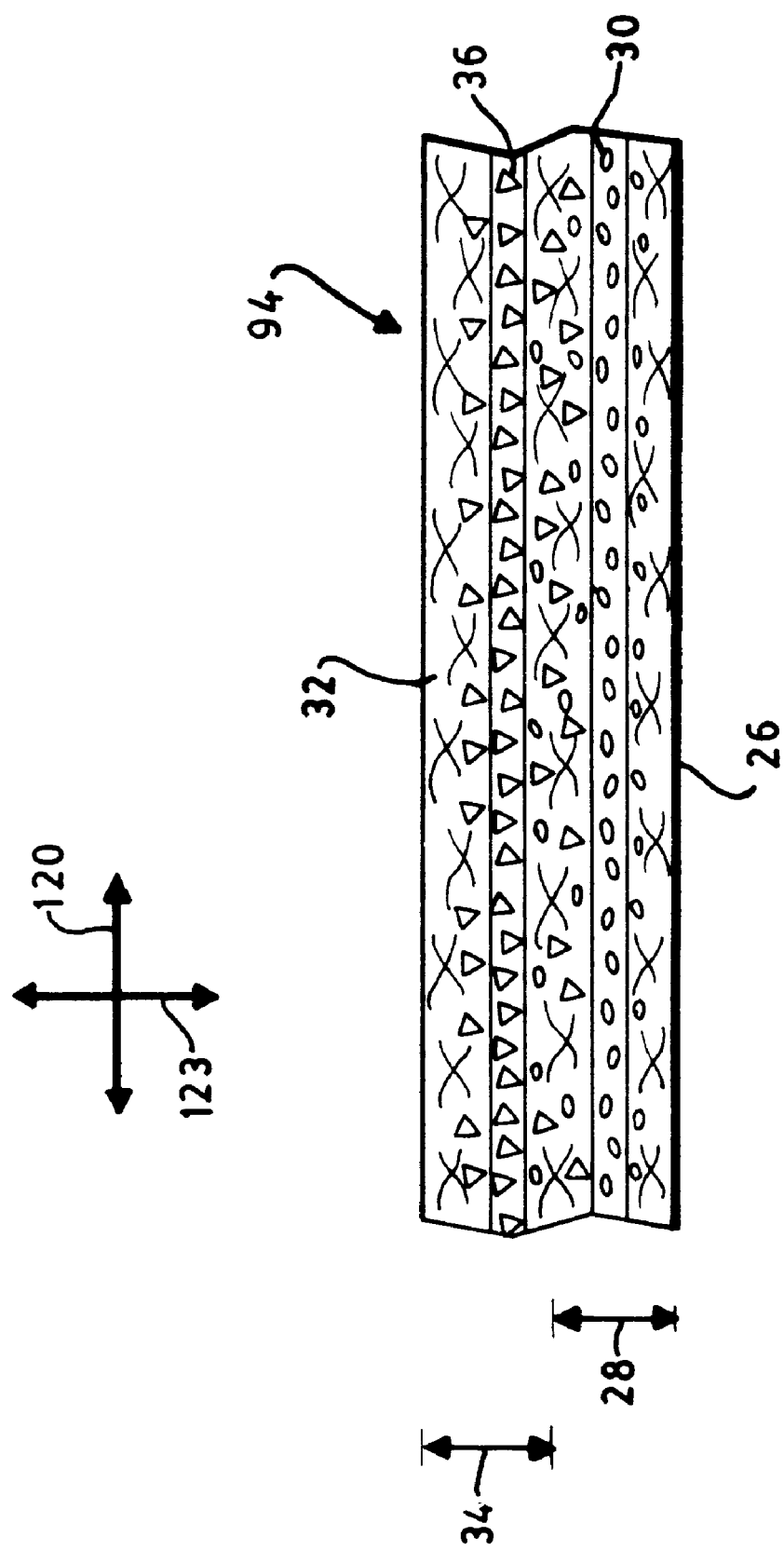
FIG. 10 representatively shows a schematic cross-sectional view of a web that can be produced with the forming system of FIG. 9.

As the rotating forming drum 64 transports the accumulating web 94 through and past the second section 84 of the forming path length, the appointed fiber material can continue to be deposited onto the moving forming surface 22. With reference to FIGS. 8 and 10 a web surface region that is rich in fiber material and poor in superabsorbent material can be formed onto the accumulating fibrous web 94. Desirably, the web surface region can be substantially free of superabsorbent material. In particular aspects of the invention, a distinctive fourth fibrous stratum 60 can be formed onto the accumulating fibrous web, as representatively shown in FIG. 12.

Figure 7:
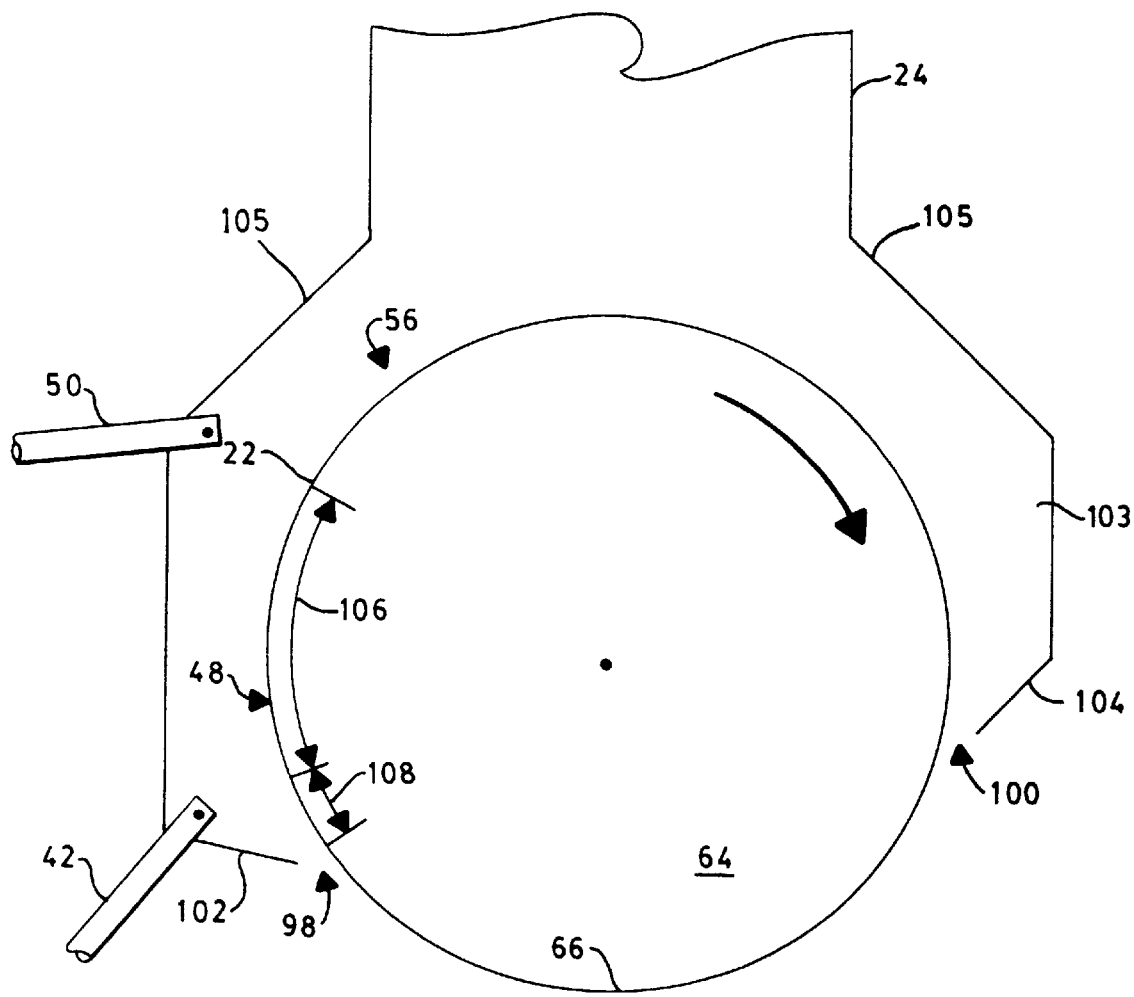
FIG. 7 representatively shows a schematic side view of a forming technique of the invention which incorporates a nozzle system having first and second nozzles.

In a desired aspect of the invention, the first nozzle 42 can be constructed and arranged to direct superabsorbent material onto a first discrete segment of the forming path length, and this first nozzle can be inwardly spaced from the forming chamber entrance 98 by a predetermined inset distance 108 (e.g. FIGS. 1 and 7). In particular aspects, the inset distance can be at least a minimum of about 1 cm. The inset distance can alternatively be at least about 10 cm, and optionally, can be at least about 15 cm to provided improved performance. In other aspects, the inset distance can be not more than a maximum of about 80 cm. The inset distance can alternatively be not more than about 60 cm, and optionally, can be not more than about 40 cm to provide improved effectiveness.

In other aspects, the inset distance can provide a path-position value (PPV) which is at least a minimum of about 1% of the forming path length 40. The PPV of the first nozzle can alternatively be at least about 3%, and optionally, can be at least about 5% of the forming path length to provide improved performance. In other aspects, the PPV can be not more than a maximum of about 25% of the forming path length. The PPV can alternatively be not more than about 19%, and optionally, can be not more than about 13% of the forming path length to provide improved operation.

By incorporating the selected inset distance 108, a stratum of fiber material can be deposited and accumulated onto the forming surface 22 prior to the incorporation of the first superabsorbent material 30. With reference to FIGS. 8 and 10 an initially formed section of the fibrous web 94 can provide an initial web surface region that is rich in fiber material and poor in superabsorbent material. Desirably, the initial surface region can be substantially free of superabsorbent material. In particular aspects of the invention, a fifth fibrous stratum 62 can be initially formed onto the forming surface 22 prior to the incorporation of superabsorbent material, as representatively shown in FIG. 12.

As the formed fibrous web exits from the forming chamber 24, a scarfing system can be employed to adjust the basis weight of the formed web. In particular arrangements, the scarfing system can include a conventional, rotatable scarfing roll 70 which is configured to contact an exposed surface of the formed, absorbent web 94 and to remove material from the web to provide a more uniform basis weight to the final web. The removed material can be directed through an appropriate, scarfing exit conduit 88 for further processing. The removed material may, for example, be recycled back into the forming chamber, may be recycled into the fiberizer, or may be directed and transported to a supplemental processing operation, as desired.

During the system operation, the formed absorbent web 94 is operatively removed from the forming surface 22 and is directed for further processing. In the representatively shown configuration, a turn roll 72 can be employed to separate the formed web 94 from the forming drum 64, and can direct the absorbent web 94 for further processing.

With reference to FIG. 2, an alternative transfer mechanism may be employed to separate the formed fibrous web 94 from the forming drum 64. As representatively shown, a transfer belt conveyor system 68 can be employed to separate the formed web 94 from the forming surface 22, and can direct the formed web 94 along the manufacturing system for further processing. The further processing may, for example, include a debulking, compressing or densifying operation. Additionally, the fibrous web 94 can be combined with other components to produce a final manufactured article. In the manufacture of a disposable absorbent garment, for example, the fibrous web can be combined with a liquid-permeable topsheet layer, a substantially liquid-impermeable backsheet layer, elastic members and fasteners, as well as other components.

Figure 3:
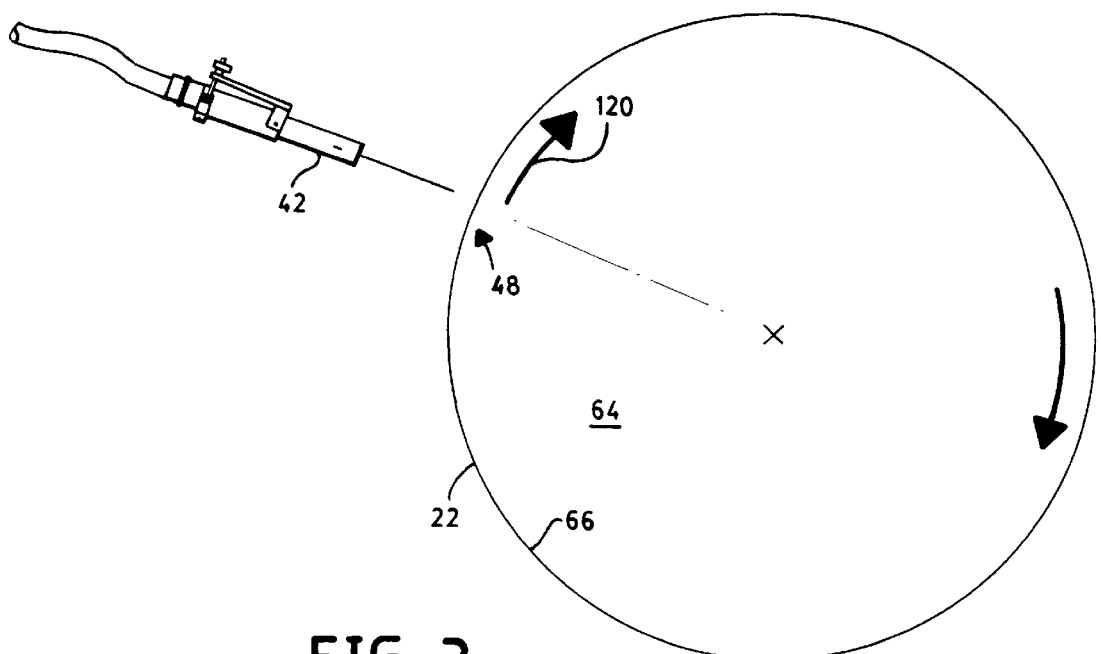
FIG. 3 representatively shows a schematic side view of a nozzle positioned with a selected, substantially zero, nozzle angle relative to the forming surface.
Figure 3A:
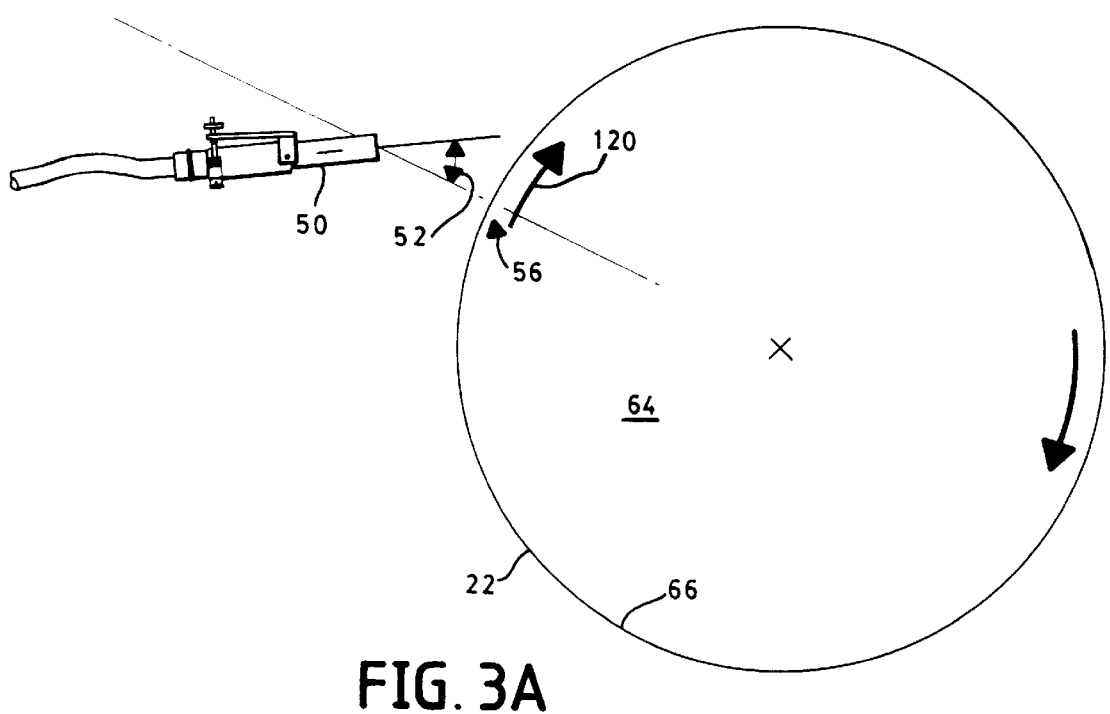
FIG. 3A representatively shows a schematic side view of a nozzle positioned with another selected nozzle angle relative to the forming surface.
Figure 3D:
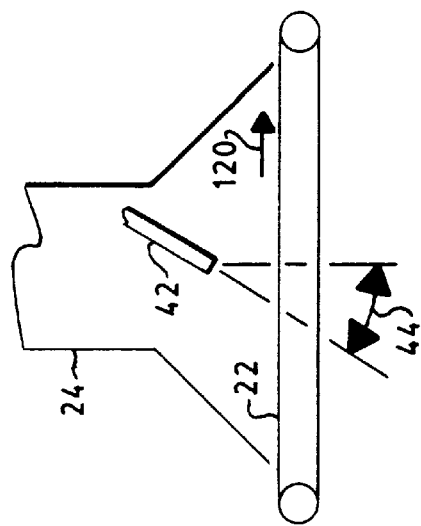
FIG. 3D representatively shows a schematic side view of an endless belt, flat screen forming system having a nozzle positioned with a negative nozzle angle.
Figure 3C:
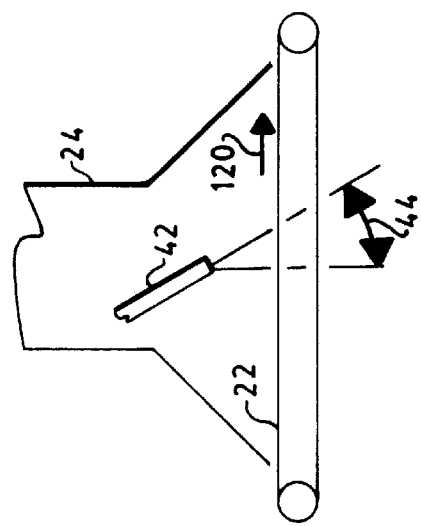
FIG. 3C representatively shows a schematic side view of an endless belt, flat screen forming system having a nozzle positioned with a positive nozzle angle.
Figure 3B:
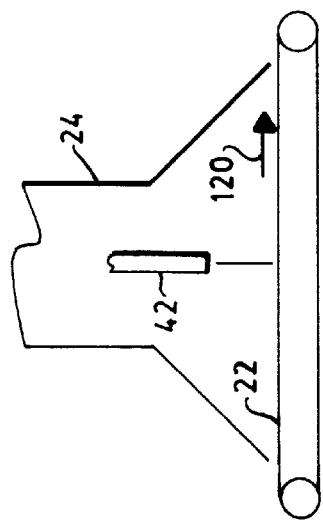
FIG. 3B representatively shows a schematic side view of a system having a substantially flat forming surface provided by an endless belt, forming screen, and having a nozzle positioned with a substantially zero, nozzle angle.

An alternative configuration of the invention can include a translating of a recirculating, endless forming belt which has an outer periphery that provides the forming surface 22 (e.g. FIG. 3B). Accordingly, the transporting of a generally flat, linearly moving section of the endless forming belt can operatively provide a moving forming surface 22 traveling through an appropriately cooperating, generally linear forming chamber. Conventional air forming systems which incorporate an endless forming belt are well known in the art. For example, conventional belt forming systems are available from the Paper Converting Machine Corp., a business having offices located in Green Bay, Wis.

Either or both of the first and second nozzle mechanisms 42 and 50 can be configured to provide a substantially continuous delivery or an intermittent delivery of their corresponding superabsorbent materials into the forming chamber. Examples of suitable systems for providing an intermittent or pulsed delivery of superabsorbent material are described in U.S. Pat. No. 5,028,224 entitled METHOD AND APPARATUS FOR INTERMITTENTLY DEPOSITING PARTICULATE MATERIAL IN A SUBSTRATE AND ARTICLE MADE THEREWITH by C. Pieper et al. which issued July 2, 1991, the entire disclosure of which is hereby incorporated by reference in a manner that is consistent herewith.

In its various configurations, the technique of the invention can include a moving of the selected forming surface 22 in the forming chamber 24 along an appointed forming path which provides an operative forming path length 40. The first fibrous stratum 26 of fiber material 96 can be deposited to overlie the forming surface 22 and the first fibrous stratum 26 can have its corresponding first stratum thickness 28. The first quantity of the first superabsorbent material 30 can be directed with a first nozzle 42 to form a first superabsorbent-rich stratum within the first stratum thickness 28 of the first fibrous stratum 26. The first nozzle may, for example, be oriented at a first nozzle tilt angle 44 relative to a first local section of the forming surface 22. The second fibrous stratum 32 of fiber material can be deposited to overlie the first fibrous stratum 26, and the second fibrous stratum 32 can have its corresponding second stratum thickness 34. The second quantity of the second superabsorbent material 36 can be directed with a second nozzle 50 to form a second, superabsorbent-rich stratum within the second stratum thickness 34 of the second fibrous stratum 32. The second nozzle 50 may, for example, be oriented at a second nozzle tilt angle 52 relative to a second local section of the forming surface 22.

In typical configurations, each of the nozzles 42 and 50 can have an associated, corresponding outlet opening that is arranged to face along an appointed direction, and the facing direction can be used to determine the predominant direction of movement of the superabsorbent particles from the nozzle outlet. Ordinarily, this substantially corresponds to movement direction at the center of the nozzle outlet. The position and orientation of each nozzle can be determined with respect to a line that is perpendicular to the local section of the forming surface. With a forming drum system, for example, the perpendicular line extends from the center of the nozzle outlet to center of the drum.

Figure 3F:
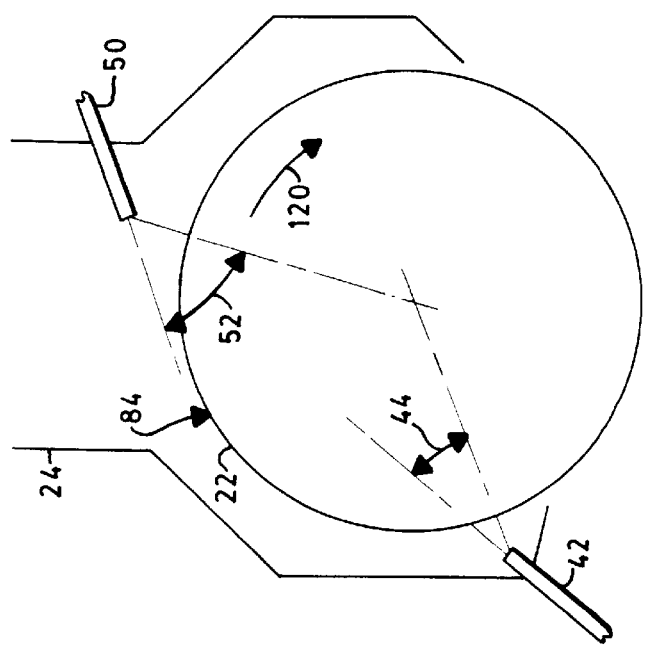
FIG. 3F representatively shows a schematic side view of a forming drum system having a first nozzle positioned with a positive nozzle angle and a second nozzle positioned with a negative nozzle angle.
Figure 3E:
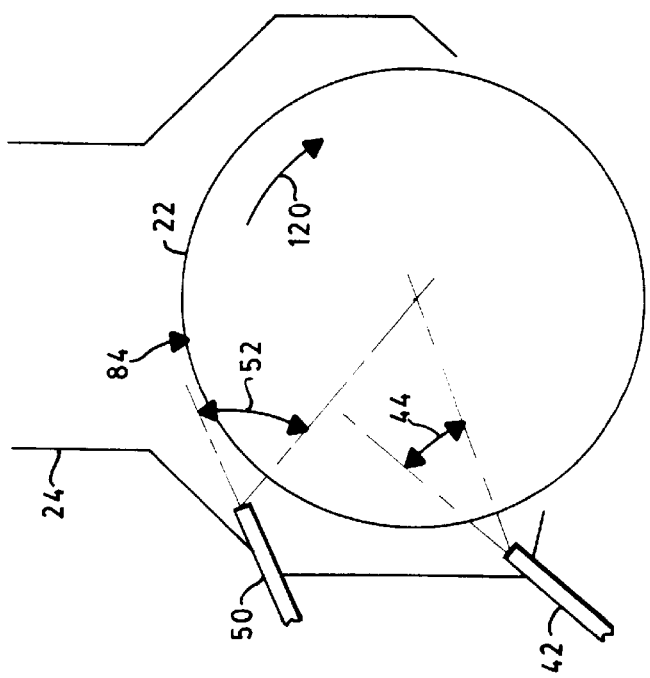
FIG. 3E representatively shows a schematic side view of a forming drum system having a first nozzle positioned with a first, positive nozzle angle and a second nozzle positioned with a second, positive nozzle angle.

As representatively shown in FIGS. 3 through 3F, each nozzle angle is an angle that is determined along the local machine-direction 120 and is measured with respect to line that is perpendicular to the local portion of the forming surface at which that nozzle is positioned. A "plus" or "positive" angle rotates or tilts the nozzle to direct material in a travel direction or trajectory that is generally more aligned along the direction of movement of the forming surface, as illustrated in FIGS. 3C and 3E. A "s" or "negative" angle rotates or tilts the nozzle to direct material in a travel direction or trajectory that is aligned generally more counter to the direction of movement of the forming surface, as representatively shown in FIGS. 3D and 3F.

In particular aspects, the first nozzle tilt angle 44 can be a minimum of at least about minus (−)56 degrees (°). The first nozzle angle can alternatively be at least about −480, and optionally, can be at least about −35° to provide an improved distribution and placement of the superabsorbent. In other aspects, the first nozzle angle 44 can be not more than a maximum of about +70°. The first nozzle angle can alternatively be not more than about +55°, and optionally, can be not more than about +35° to provide further improved effectiveness.

In additional aspects, the second nozzle tilt angle 52 can be at least a minimum of −35°. The second nozzle angle can alternatively be at least about −26°, and optionally, can be at least about −15° to provide an improved distribution and placement of the superabsorbent. In other aspects, the second nozzle angle 52 can be not more than a maximum of about +55°. The second nozzle angle can alternatively be not more than about +45°, and optionally, can be not more than about +40° to provide further improved effectiveness.

If the tilt angle of a selected nozzle is too low or too high, it can be excessively difficult to accurately control and direct the superabsorbent material to a desired location within the thickness of a selected fibrous stratum. Additionally, the deposited superabsorbent material may not be adequately concentrated within its appointed fibrous stratum.

Where a selected nozzle (e.g. nozzle 42 or 50) is arranged to direct and deposit its corresponding quantity of superabsorbent material onto its appointed portion of the forming surface or forming path length, the selected nozzle may incorporate a positive or negative nozzle angle, depending upon its relative location within the forming chamber 24 and its relative location along the forming path length 40. With reference to FIG. 3E, for example, the second nozzle 50, can be located towards the chamber entrance and aligned with a positive nozzle angle to direct and deposit its corresponding quantity of superabsorbent material onto the portion of the forming surface 22 which is located along a second section 84 of the forming path and substantially corresponds to a second 25% of the forming path length. With reference to FIG. 3F, the second nozzle 50, can optionally be located more towards the chamber exit and aligned with a negative nozzle angle to direct and deposit its corresponding quantity of superabsorbent material onto the portion of the forming surface 22 that is located along the second section of the forming path and substantially corresponds to the second 25% of the forming path length.

In desired configurations, each of the nozzles 42 and/or 50 may be arranged and aligned with its corresponding nozzle angle positioned to have a relatively more perpendicular orientation relative to their corresponding local sections 48 and 56, respectively, of the forming surface 22. As a result, each nozzle can provide a distribution of superabsorbent material within and through a relatively short distance along the thickness dimension of its corresponding fibrous stratum 26 or 32, respectively. Where a selected superabsorbent nozzle is aligned and positioned to be relatively more tangential to its corresponding local section of the forming surface 22 (e.g. FIG. 3A), the technique of the invention can be adjusted to provide a distribution of the corresponding superabsorbent material within and through a longer distance along the thickness dimension 28 or 34 of the corresponding fibrous stratum 26 or 32, respectively.

Depending upon the selected objectives of a desired configuration of the invention, when a nozzle tilt angle 44 or 52 is rotated close to or beyond a line that is parallel to a local tangent of the forming surface, the superabsorbent material dispensed by its corresponding nozzle 42 or 50 may be distributed along an excessively large length of the web thickness. Additionally, the dispensed superabsorbent will not be sufficiently concentrated within its corresponding strata of the web. If the nozzle angle 44 or 52 approaches a line that is perpendicular to a local tangent of the forming surface, the superabsorbent material deposited by its corresponding nozzle 42 or 50 can be distributed along a shorter length of the web thickness. Additionally, the dispensed superabsorbent will be less mixed or dispersed with fibrous material within its corresponding strata of the web. Again depending upon the selected objectives of a desired configuration of the invention, when the nozzle angle 44 or 52 approaches a line that is perpendicular to a local tangent of the forming surface, the superabsorbent material deposited by its corresponding nozzle 42 or 50 may be distributed along too short a length of the web thickness. Additionally, the dispensed superabsorbent be insufficiently mixed or dispersed with fibrous material within its corresponding strata of the web. Thus, the thickness dimension occupied by the deposited superabsorbent material and the degree of mixing or dispersion can, for example, be advantageously controlled by adjusting the nozzle tilt angle 44 and/or 52.

In particular aspects, a selected forming system (e.g. a rotatable drum former) can, for example, have a forming path length of approximately 3.2 m. The first nozzle 42 can have a path-position value (PPV) of at least about 3%, and a nozzle tilt angle of not more than about +70°. The first nozzle can alternatively have a PPV of at least about 5%, and a nozzle tilt angle of not more than about +54°. Optionally, the first nozzle can alternatively have a PPV of at least about 7%, and a nozzle tilt angle of not more than about +37°. Additionally, the first nozzle 42 can have a path-position value (PPV) of not more than about 30%, and a nozzle tilt angle of at least about 8°. The first nozzle can alternatively have a PPV of not more than about 20%, and a nozzle tilt angle of at least about −55°. Optionally, the first nozzle can alternatively have a PPV of not more than about 12%, and a nozzle tilt angle of at least about −13°.

In further aspects, the second nozzle 50 can have a path-position value of at least about 20% (e.g. with a forming path length of approximately 3.2 m), and a nozzle tilt angle of not more than about +55°. The second nozzle can alternatively have a PPV of at least about 24%, and a nozzle tilt angle of not more than about +52°. Optionally, the second nozzle can alternatively have a PPV of at least about 28%, and a nozzle tilt angle of not more than about +41°. Additionally, the second nozzle 50 can have a path-position value of not more than about 63%, and a nozzle tilt angle of at least about −26°. The second nozzle can alternatively have a PPV of not more than about 50%, and a nozzle tilt angle of at least about −35°. Optionally, the second nozzle can alternatively have a PPV of not more than about 37%, and a nozzle tilt angle of at least about −15°.

Figure 4:
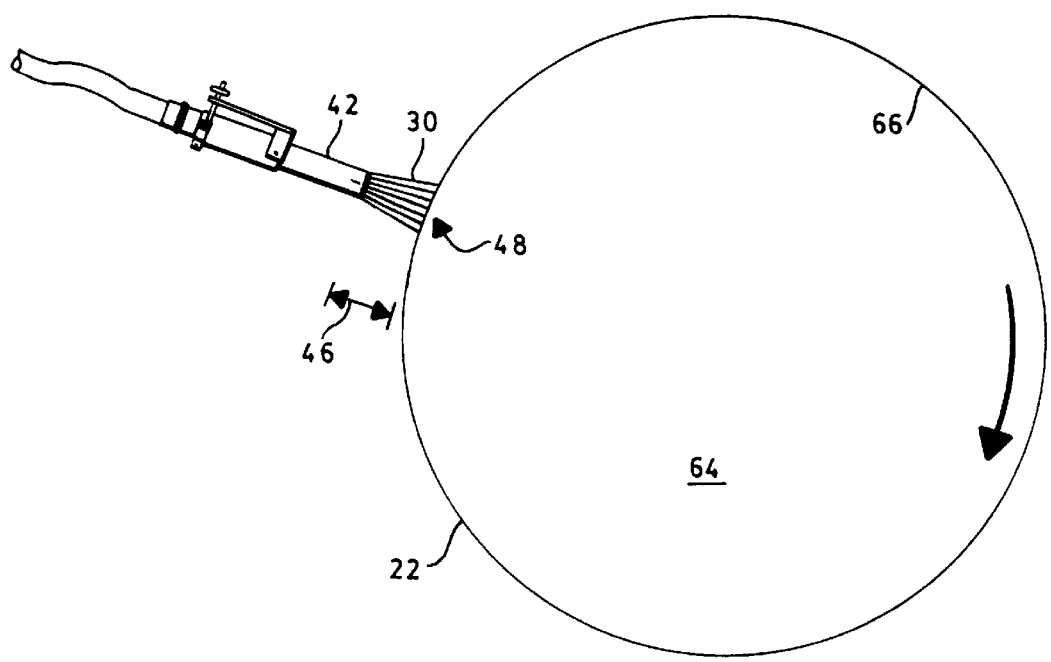
FIG. 4 representatively shows a schematic side view of a nozzle positioned with a selected nozzle distance relative to the forming surface.
Figure 4A:
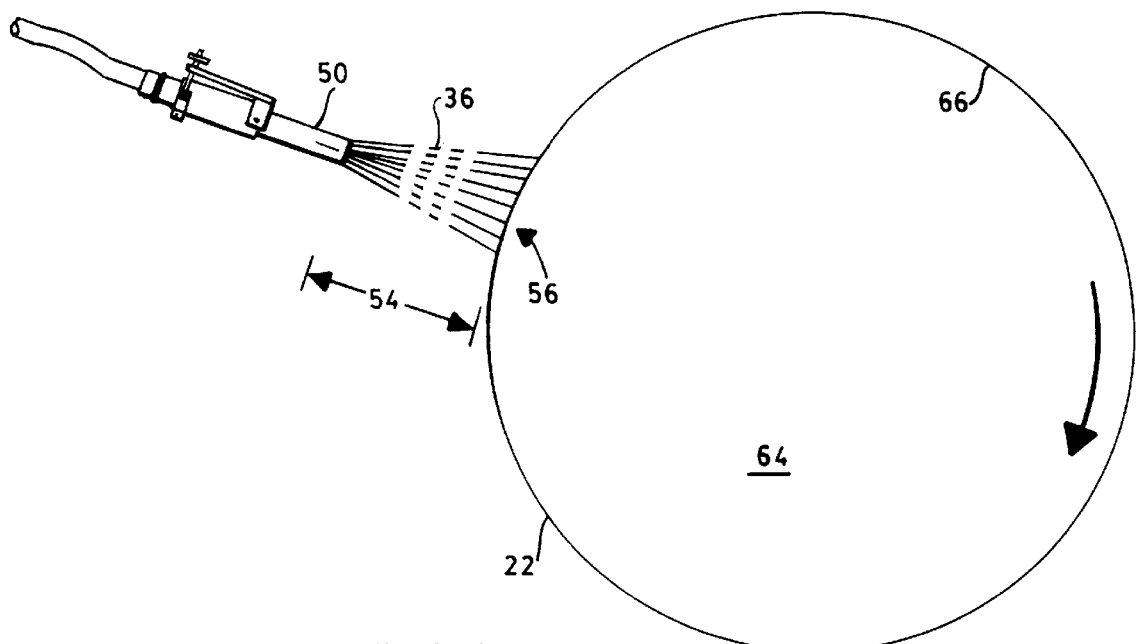
FIG. 4A representatively shows a schematic side view of a nozzle positioned with another selected nozzle distance relative to the forming surface.
Figure 5:
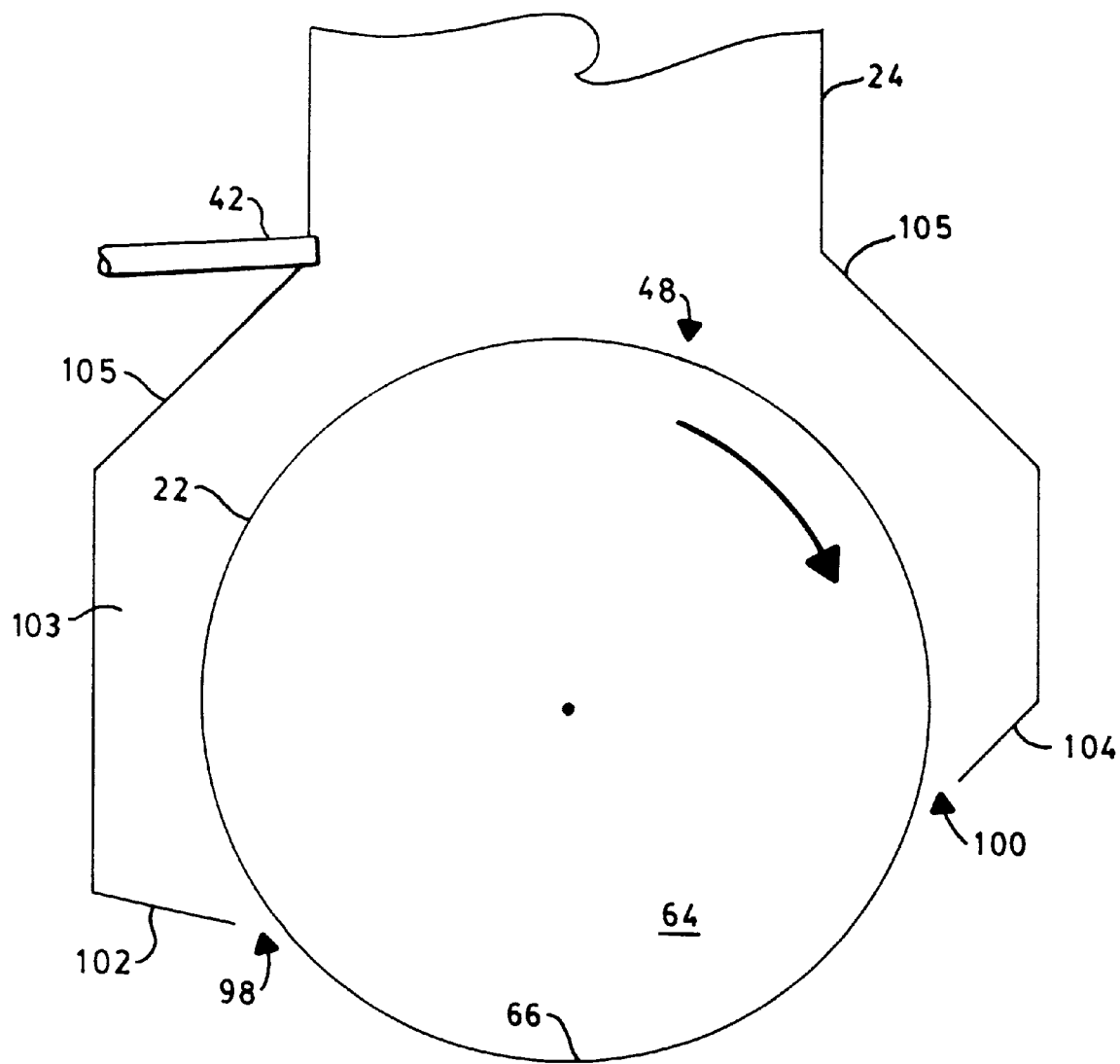
FIG. 5 representatively shows a schematic side view of a forming technique of the invention which incorporates a rotatable forming drum and a single nozzle system.

In still another aspect, each of the nozzles can be distinctively located at a selected height distance away from the forming surface 22. For example, the first nozzle can be positioned above its corresponding local section 48 of the forming surface 22. In particular configurations, the first nozzle distance 46 can be at least a minimum of about 2 cm, as representatively shown in FIGS. 4 and 4A. The first nozzle distance can alternatively be at least about 10 cm, and optionally, can be at least about 25 cm to provide improved performance. In other aspects, the first nozzle distance 46 can be not more than a maximum of about 100 cm. The first nozzle distance can alternatively be not more than about 75 cm, and optionally, can be not more than about 50 cm to provide desired effectiveness.

The second nozzle 50 can similarly be positioned at a second, nozzle height distance 54 away from its corresponding local section 56 of the forming surface 22. For example, the second nozzle can be positioned above its corresponding local section 56 of the forming surface 22. In particular aspects, the second nozzle distance 54 can be at least a minimum of about 2 cm. The second nozzle distance 54 can alternatively be at least about 10 cm, and optionally, can be at least about 25 cm to provide improved performance. In other aspects, the second nozzle distance 54 can be not more than a maximum of about 200 cm. The second nozzle distance 54 can alternatively be not more than about 100 cm, and optionally, can be not more than about 50 cm to provide desired effectiveness.

The nozzle distances 46 and 54 can advantageously be adjusted to selectively regulate the distribution of corresponding superabsorbent material through their corresponding fibrous strata 26 and 32, respectively. Where the nozzle is positioned with a nozzle distance which is relatively closer to its corresponding local section of the forming surface 22, the associated superabsorbent material can be distributed along a relatively smaller length of the thickness dimension 28 or 34 of the first fibrous stratum 26 or the second fibrous stratum 32, respectively. If the nozzle height distance 46 or 54 is too small, the corresponding nozzle may interfere with the movement of the web 94 through the forming chamber, or the momentum of its injected superabsorbent material will excessively displace the fiber material away from the forming surface 22. Additionally, the superabsorbent material may be overly concentrated and insufficiently mixed with the fiber material in its appointed stratum. If the nozzle height distance 46 or 54 is too large, the corresponding nozzle will provide an insufficient concentration of superabsorbent material within its appointed superabsorbent-containing stratum. Thus, the thickness dimension occupied by the deposited superabsorbent material and the degree of mixing or dispersion can advantageously be further controlled by adjusting the nozzle height distance 46 or 54.

Another aspect of the invention can include a directing of the first quantity of superabsorbent material to deliver the superabsorbent material into the forming chamber 24 at a first superabsorbent injection speed. Additionally, the directing of the second quantity of superabsorbent material can be configured to deliver the superabsorbent material into the forming chamber 24 at a second superabsorbent injection speed.

The first superabsorbent speed can be at least a minimum of about 15 m/sec. The first superabsorbent speed can alternatively be at least about 25 m/sec, and optionally, can be at least about 30 m/sec to provide improved performance. In other aspects, the first superabsorbent speed can be not more than a maximum of about 70 m/sec. The first superabsorbent speed can alternatively be not more than about 50 m/sec, and optionally, can be not more than about 35 m/sec to provide improved effectiveness.

In a similar aspect, the second superabsorbent speed can be at least a minimum of about 15 m/sec. The second superabsorbent speed can alternatively be at least about 25 m/sec, and optionally, can be at least about 30 m/sec to provide improved performance. In other aspects, the second superabsorbent speed can be not more than a maximum of about 70 m/sec. The second superabsorbent speed can alternatively be not more than about 50 m/sec, and optionally, can be not more than about 35 m/sec to provide improved effectiveness.

An appropriate regulation of the superabsorbent speed can provide an adjusted speed which provides a more consistent delivery of superabsorbent particles and a reduced variation in the amount of superabsorbent added to the appointed stratum of the web 94. The selected superabsorbent speed and direction imparts sufficient energy and momentum to operatively control the injection path and trajectory of the superabsorbent particles and to control the distribution of the superabsorbent particles into their corresponding, appointed strata. If the superabsorbent speed is too low, the primary airflow which transports the fibers through the forming chamber can excessively dominate and control the movement of the superabsorbent material into the formed web. If the superabsorbent speed is too high, the superabsorbent particles may penetrate too deeply into the laid fiber material or may excessively displace the fibrous material away from the forming surface. Additionally, an excessive superabsorbent speed may cause the superabsorbent material to bounce or skip off the targeted area of the fibrous material and land elsewhere, at an undesired region of the web.

With reference to FIGS. 5 and 6, the technique of the invention can be constructed and arranged to generate a conventional web 94 having a web thickness 28. The web can include a substantially uniform mixture of fibers 96 and superabsorbent particles 30 within a fibrous stratum 26.

With reference to FIG. 7, the process and apparatus of the invention can, for example, be configured with the first nozzle 42 having a path-position value (PPV) of 8.5%, a nozzle tilt angle of +29°, and nozzle height of 7 inches (17.8 cm). Additionally, the second nozzle 50 can have a PPV of 30%, a nozzle tilt angle of +35°, and nozzle height of 8.5 inches (21.6 cm).

Accordingly, the process and apparatus can generate a first fibrous stratum 26 having a first superabsorbent material 30 that is more concentrated within a relatively short distance along the thickness 28 of the first stratum 26, as representatively shown in FIG. 8. Additionally, the process and apparatus can generate a second fibrous stratum 32 having a first superabsorbent material 36 that is more concentrated within a relatively short distance along the thickness 34 of the second stratum 32.

With reference to FIG. 9, another example of the process and apparatus of the invention can be configured with the first nozzle 42 having a PPV of 10%, a nozzle tilt angle of 53°, and nozzle height of 7 inches (17.8 cm). Additionally, the second nozzle 50 can have a PPV of 36%, a nozzle tilt angle of +39°, and nozzle height of 8.7 inches (22.1 cm).

Accordingly, the process and apparatus can generate a first fibrous stratum 26 having a first superabsorbent material 30 that is more diffusely distributed within a relatively longer distance along the thickness 28 of the first stratum 26, as representatively shown in FIG. 10. Additionally, the process and apparatus can generate a second fibrous stratum 32 having a first superabsorbent material 36 that is more diffusely distributed within a relatively longer distance along the thickness 34 of the second stratum 32. In some desired arrangements, there may be some overlap of the first superabsorbent material into the second fibrous stratum, and/or some overlap of the second superabsorbent material into the first fibrous stratum.

In a further example, the process and apparatus of the invention can have the arrangement representatively shown in FIG. 11. The system can be configured with a curved first nozzle 42 having a designated PPV of 12%, a designated tilt angle of −15°, and a nozzle height of 3 inches (7.6 cm). Additionally, the second nozzle 50 can have a PPV of 36%, a nozzle tilt angle of +65°, and nozzle height of 4.4 inches (11.2 cm).

Accordingly, the process and apparatus can generate a first fibrous stratum 26 having a first superabsorbent material 30 that is more uniformly distributed within and along the thickness 28 of the first stratum 26, as representatively shown in FIG. 12. Additionally, the process and apparatus can generate a second fibrous stratum 32 having a first superabsorbent material 36 that is more uniformly distributed within and along the thickness 34 of the second stratum 32.

In a further aspect, the technique of the invention can include a depositing of a third fibrous stratum 58 of fiber material at a location which is interposed between the first fibrous stratum 26 and the second fibrous stratum 32. With reference to the example illustrated in FIG. 12, the third fibrous stratum 58 can be relatively superabsorbent-poor, as compared to its adjacent superabsorbent-rich strata, and may optionally be substantially free of superabsorbent material. In particular aspects, the third fibrous stratum 58 can contain an amount, such as a basis weight amount, of superabsorbent material which is less than the amount of superabsorbent material in the first fibrous stratum 26.

Additionally, the amount of superabsorbent in the third fibrous stratum can be relatively less than the amount of superabsorbent material in the second fibrous stratum 32.

A further aspect of the invention can include a depositing of a fourth fibrous stratum 60 of fiber material to overlie the second fibrous stratum 32. As representatively shown in the example illustrated in FIG. 12, the fourth fibrous stratum 60 can be positioned adjacent to a surface of the second fibrous stratum 32 which is opposite of and spaced from the location of the first fibrous stratum 26. In desired arrangements, the fourth fibrous stratum 60 can be superabsorbent-poor, as compared to its adjacent superabsorbent-rich strata. In particular aspects, the amount of superabsorbent material in the fourth fibrous stratum 60 can be relatively less than the amount of superabsorbent material in the second fibrous stratum 32, and in further aspects, the fourth fibrous stratum can be substantially free of superabsorbent material.

Yet another aspect of the invention can include a depositing of a fifth fibrous stratum 62 of fiber material to lie adjacent a surface of the first fibrous stratum 26 which is opposite from and spaced from the second fibrous stratum 32. With reference to the example representatively shown in FIG. 12, the fifth fibrous stratum can be superabsorbent-poor, as compared to its adjacent superabsorbent-rich strata. In particular arrangements, the amount of superabsorbent in the fifth fibrous stratum can be relatively less than the amount of superabsorbent material in the first fibrous stratum 26. In other arrangements, the fifth fibrous stratum can be substantially free of superabsorbent material.

It should be readily appreciated that the superabsorbent materials can be provided in various types and in various combinations of types. In a particular aspect, the second superabsorbent material 36 can be provided in a physical or chemical configuration which is substantially equivalent to a physical or chemical configuration of the first superabsorbent material 30. Alternatively, the second superabsorbent material can have a configuration which differs from the configuration of the first superabsorbent material 30.

In a particular arrangement, the second superabsorbent material 36 can have a composition which is substantially the same as a composition of the first superabsorbent material 30. Alternatively, the second superabsorbent material 36 can have a composition which differs from the composition of the first superabsorbent material 30. Additionally, the first superabsorbent material can have an associated first set of absorbent properties, and the second superabsorbent material can have an associated second set of absorbent properties which differ from the properties of the first superabsorbent material.

With reference to FIGS. 11A and 11B, at least one of the nozzles 42 and/or 50 can be a hooked nozzle that generates a relatively abrupt change in the direction of movement of the superabsorbent material as the superabsorbent travels through the end of the nozzle and exits the nozzle outlet. For example, the hooked nozzles representatively shown in FIG. 11A may include a deflector plate 80 mounted at the end of its associated nozzle. The moving superabsorbent material impacts the end plate 80, and experiences a reduction or other change in speed, and undergoes a rapid change in movement direction. As a result, the superabsorbent material can fall or otherwise exit through a "sideward" outlet and be directed toward the forming surface 22. Another hooked nozzle, representatively shown in FIG. 11B, incorporates a bent hook which abruptly curves toward the forming surface 22. When the moving superabsorbent material enters the bent hook section of the nozzle, the superabsorbent experiences a change in speed and a rapid change in movement direction. As a result, the superabsorbent material exits through an end-outlet from the bent hook section, and is directed toward the forming surface 22. In particular aspects, the first hooked nozzle 42 can, for example, have a path-position value of 30% and a nozzle angle of −56°. The second hooked nozzle 50 can additionally have a path-position value of 50% and a nozzle angle of +17°.

With reference to FIGS. 11 and 13, at least one of the nozzles 42 and/or 50 can be a distinctively curved nozzle 86. The generally J-shape or tusk-shape configuration of the longitudinally arcuate, curved nozzle can help to provide desired distributions of the corresponding superabsorbent material within its appointed fibrous stratum of the web 94. In particular configurations, the curved nozzle can provide a more uniform or homogeneous distribution of the superabsorbent material through the z-directional, thickness dimension of the appointed stratum. The nozzle 86 can more effectively deliver the superabsorbent material over a longer length of the forming path, and can be constructed and arranged to better regulate the amount of superabsorbent delivered along individual portions of the forming path as the forming surface 22 moves through the forming chamber 24. For example, the bent, curved nozzle can advantageously deliver the superabsorbent material over a longer length of the forming path while maintaining a controlled range of nozzle spacing distances between the forming surface and the outlet openings of the curved nozzle. As representatively shown, a longitudinal length dimension of the curved nozzle 86 is preferably, generally aligned along the appointed direction of movement of the forming surface 22.

The nozzle 86 is configured with an arcuate, curved bend having a selected bend radius of curvature 110. The longitudinal, length-wise bend in the nozzle 86 curves along the travel path of the superabsorbent material, and curves away from the forming surface 22. The nozzle curvature causes the moving superabsorbent material in the nozzle to accumulate and concentrate towards and along the inside surface of the radially outboard, longitudinally arcuate wall 87 of the nozzle. As observed along the radius of curvature 110 of the nozzle 86, the radially outboard wall 87 of the nozzle is relatively farther from the center of curvature, as compared to the radially inboard wall 85 of the curved nozzle. As the particles of superabsorbent material enter the outwardly convex arc of the curved portion of the nozzle 86, the particles tend to move and concentrate towards the inside surface of the radially outboard wall of the nozzle due to the centripetal acceleration imparted by the curved nozzle. The superabsorbent material can then be discharged out from the nozzle through an array of outlet apertures 118. The particles can advantageously be discharged along the arc length of the nozzle bend, and can be discharged over a larger length and/or area dimension of the forming surface. As representatively shown, the end of the nozzle may be closed with an end cap 116.

Figure 14:
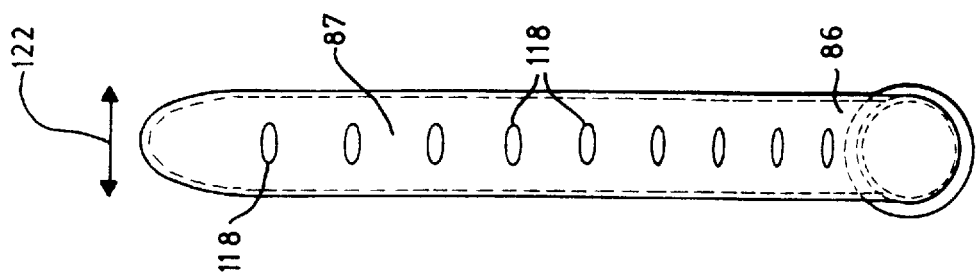
FIG. 14 representatively shows a schematic side view of a curved nozzle which includes a system of slot apertures.
Figure 14:
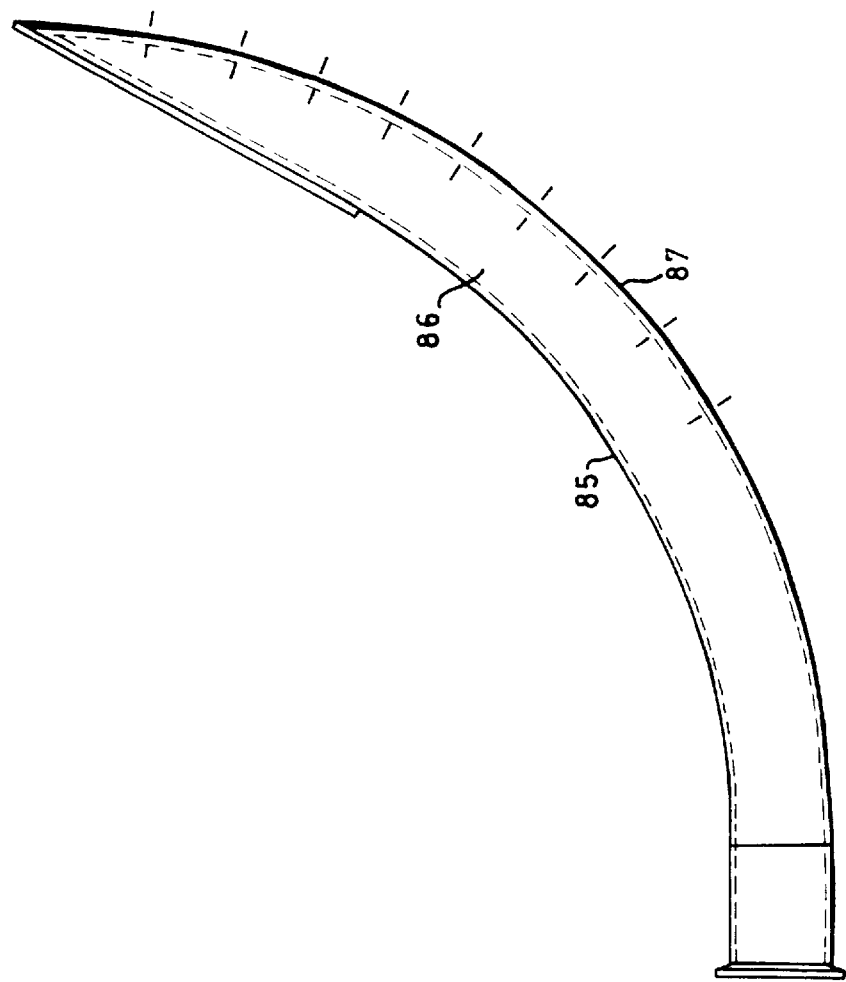
Figure 15:
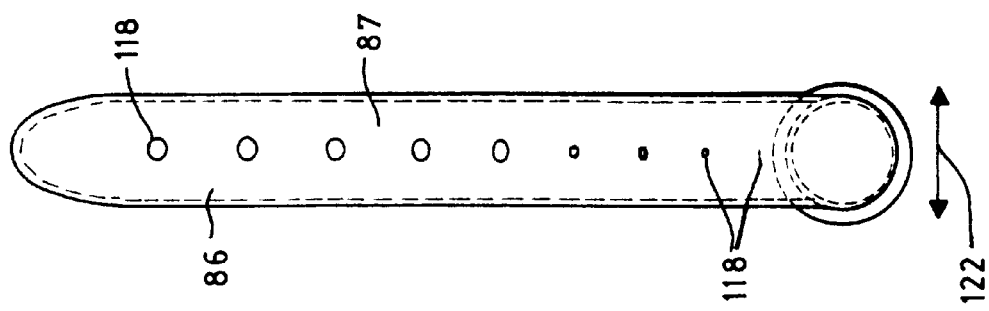
FIG. 15 representatively shows a schematic side view of a curved nozzle which includes a system of apertures having different sizes.
Figure 15:
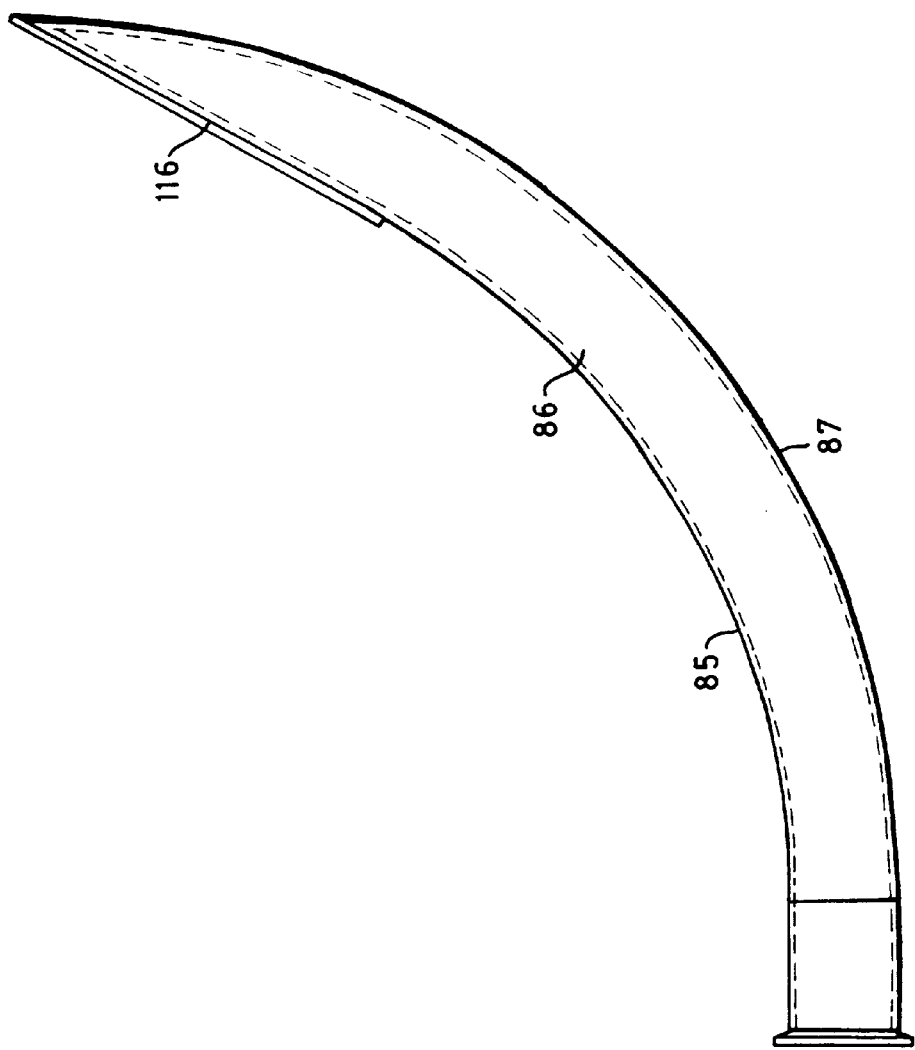
Figure 16:
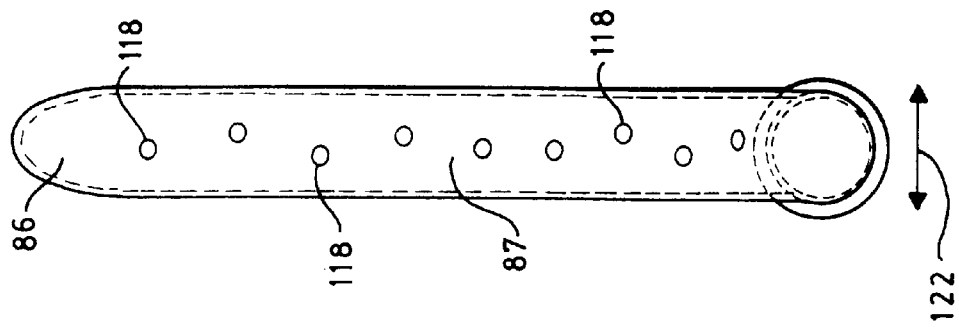
FIG. 16 representatively shows a schematic side view of a curved nozzle which includes a system of apertures which are unevenly spaced along the length of the curved nozzle.
Figure 16B:
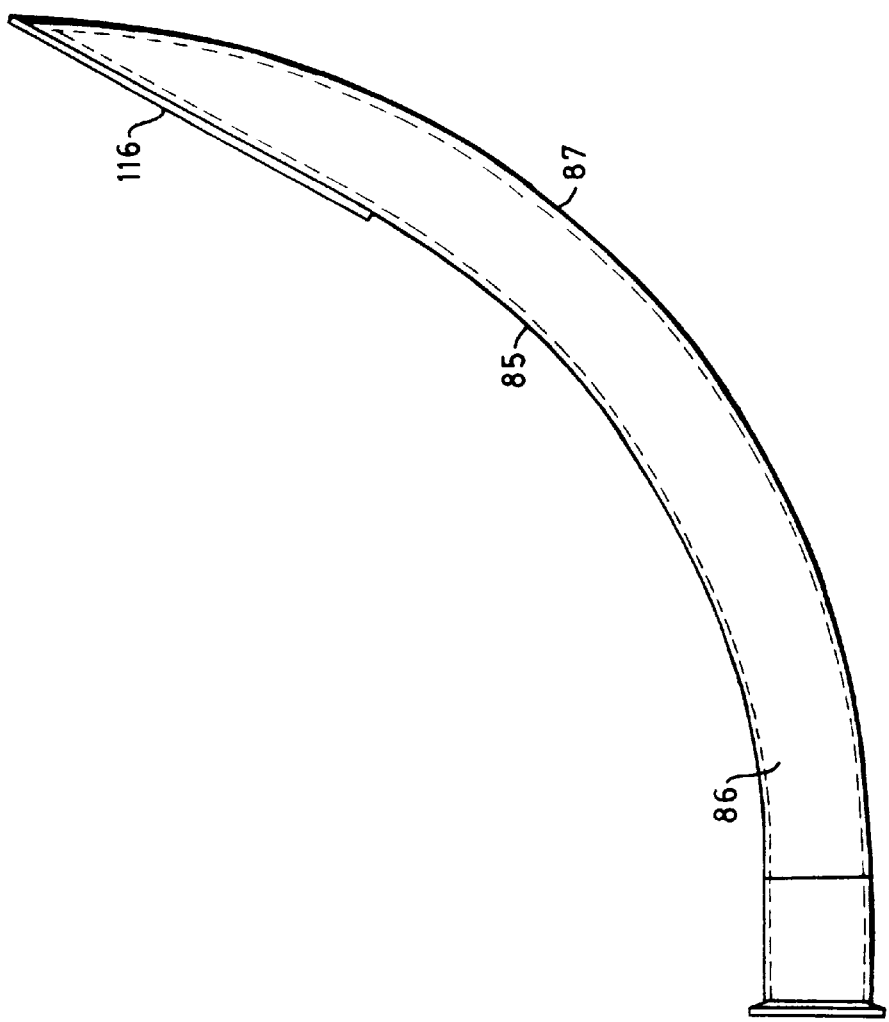
FIG. 16B representatively shows a schematic side view of a curved nozzle which includes a system of apertures which are in a staggered, non-aligned configuration along the length of the curved nozzle.
Figure 19A:
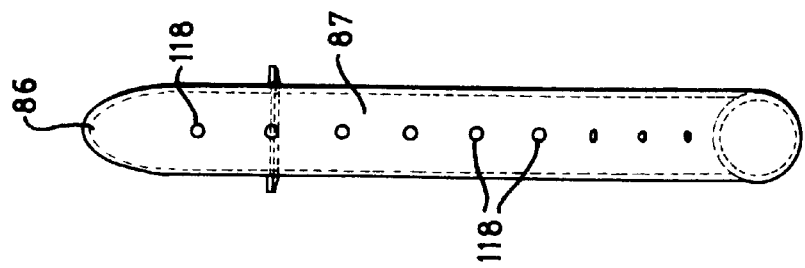
FIG. 19A representatively shows a schematic end view of the curved nozzle of FIG. 19.
Figure 19:
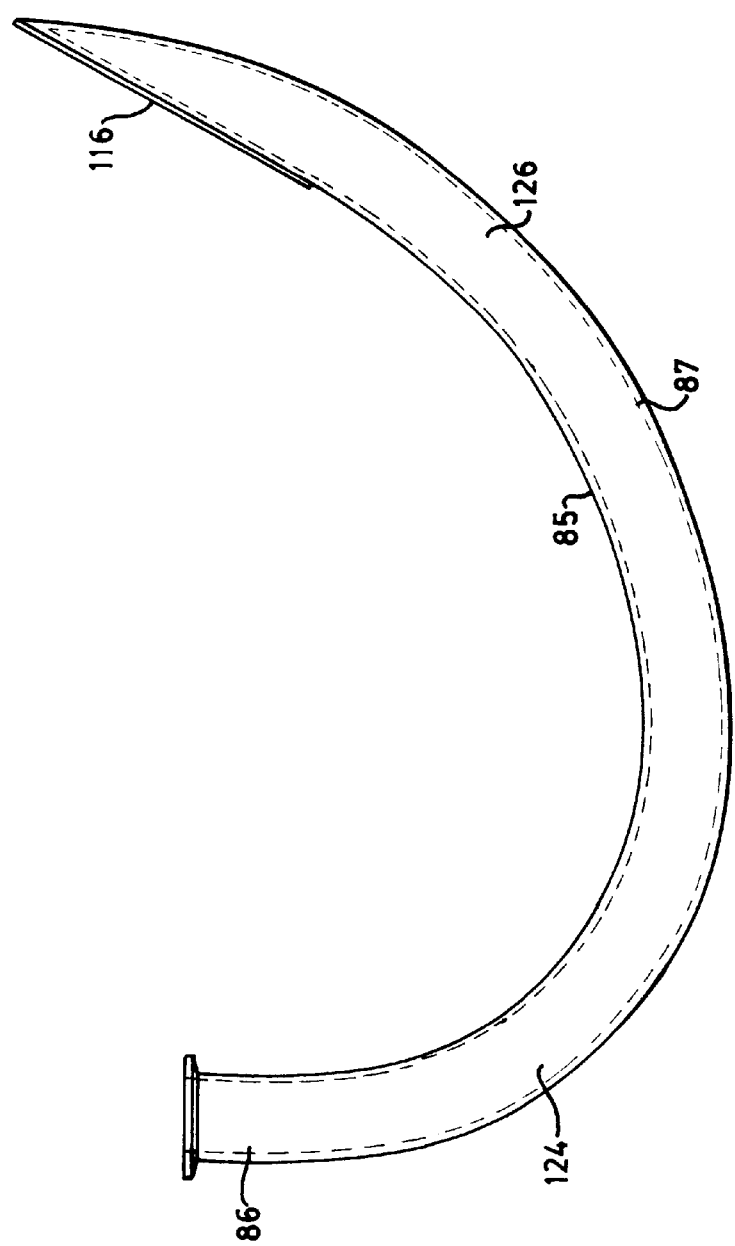
FIG. 19 representatively shows a schematic side view of a curved nozzle which includes a system of nozzle conduits, each of which is bent along a different radius of curvature.

As one moves along the curved length of the nozzle 86, the radius of curvature of the nozzle may be non-uniform and varying. The curved nozzle can have a first conduit section with a first radius of curvature, and a second conduit section with a second radius of curvature which is greater than said first radius of curvature (e.g. FIG. 19). The radius of curvature may alternatively be substantially uniform and constant along approximately the entire curved length. In particular aspects of the invention, the nozzle radius of curvature 110 can be at least a minimum of about 2.54 cm (about 1 inch). The nozzle radius of curvature can alternatively be at least about 17.8 cm (7 inch), and optionally, can be at least about 23 cm (about 9 inch) to provide improved performance. In other aspects, the nozzle radius of curvature can be not more than a maximum of about 305 cm (about 120 inch). The nozzle radius of curvature can alternatively be not more than about 64 cm (25 inch), and optionally, can be not more than about 51 cm (about 20 inch) to provide improved effectiveness. With reference to the curved nozzle representatively shown in FIG. 13, for example, the curvature radius is about 25.4 cm, and with reference to the curved nozzle representatively shown in FIG. 14, the curvature radius is about 45.7 cm (about 18 inch).

If the radius of the bend curvature is too small, the area of the forming surface onto which the superabsorbent is discharged and deposited will be too small. Desirably, the curved nozzle is configured to increase the area onto which the superabsorbent is deposited. If the radius of curvature is too large, the superabsorbent material will not be subjected to a desired level of centripetal acceleration, and will not sufficiently concentrate toward the radially outboard, wall surface of the curved nozzle.

In other aspects of the invention, the nozzle curvature can extend along a curved arc length 112 which can be at least a minimum of about 3 cm. The curved arc length can alternatively be at least about 10 cm , and optionally, can be at least about 20 cm to provide improved performance. In other aspects, the curved arc length can be not more than a maximum of about 80 cm. The curved arc length can alternatively be not more than about 60 cm, and optionally, can be not more than about 40 cm to provide improved effectiveness.

In further aspects, the arc length of the curved nozzle 86 can bend through a selected arc angle. As representatively shown in FIG. 13, the curved nozzle can bend through an arc angle of up to about 90° or more, and as representatively shown in FIG. 13B, the curved nozzle can bend through an arc angle of up to about 180° or more, If the curved arc length is too short, the area of the forming surface onto which the superabsorbent is discharged and deposited will be too small. If the curved arc length is too large, the superabsorbent material may not be adequately positioned or concentrated within the desired length of thickness of its corresponding fibrous stratum. Additionally, the curved nozzle may require excessive space in the forming chamber.

For the purposes of the present disclosure, the bend radius of curvature and the arc length of the curved nozzle are determined with respect to the radially outermost wall of the curved nozzle. Additionally, the nozzle arc length is determined with respect the circumferentially first and last outlet apertures in the curved nozzle 118*a* and 118*b*, respectively.

The selected array of outlet apertures 118 can be constructed and distributed in a predetermined pattern along the radially outboard wall of the nozzle 86, and the pattern array may have a regular or irregular arrangement. In particular aspects, the final outlet from each aperture can represent a corresponding, individual outlet discharge angle and individual outlet discharge height distance. The distribution of the superabsorbent material within its corresponding stratum of the web 94 can, for example, be regulated by selectively modifying the shapes, sizes, locations and/or distributions of the apertures 118, as well as by varying combinations thereof. For example, the apertures may be substantially circular holes (e.g. FIGS. 13 through 13C), non-circular holes, slots or the like, as well as combinations thereof. The slot apertures representatively shown in FIGS. 14 and 14A, for example, can have their longer dimensions generally aligned along the cross-direction 122, and can be configured to better regulate the particulate distribution, such as by increasing or decreasing the cross-directional width of the web 94 over which the particulate material is deposited. In other aspects, the apertures can be substantially equal in size or may be different in size to control the amount of particles deposited at selected locations along the forming path length. For example, the aperture nearest the forming chamber entrance 98 could be the smallest in size with the smallest open area, and each subsequent aperture could gradually increase in size with incrementally greater open areas, as representatively shown in FIGS. 15 and 15A. As a result, the curved nozzle can better control the distribution and concentration of particulate material along the thickness dimension of the corresponding stratum that contains the particles.

In other aspects, the apertures may be substantially regularly or evenly spaced along the curved nozzle (e.g. FIGS. 14 and 14A), or may be irregularly or unevenly spaced along the nozzle (e.g. FIGS. 16 and 16A). The chosen spacing can help to regulate the concentration of particulate material along the thickness dimension of the corresponding particulate-rich stratum. Additionally, the apertures may be substantially aligned along the curved length of the nozzle 86, or may be non-aligned. For example the apertures may be configured in a generally zigzag pattern, as representatively shown in FIGS. 16B and 16C. The non-aligned pattern can, for example, help to increase the distribution of particles along the cross-direction of the forming surface.

In further aspects of the invention, the nozzle conduit can employ other non-circular cross-sectional shapes. For example, the nozzle pipe may have an elliptical or oval cross-sectional shape, with the longer axis of the cross-section generally aligned along the nozzle radius of curvature. With reference to FIGS. 17 through 17B, the cross-section of the curved nozzle 86 may have a generally oval shape. The selected non-circular shape can help to better concentrate the particulate material toward the inside wall surface along the outward-side of the bend curvature.

Still further aspects of the invention can include an outlet extension member 128 operatively joined to the curved nozzle 86 at one or more of the apertures 118 to further regulate the direction of travel of the particulate material discharged from the apertures, as representatively shown in FIGS. 18 and 18A. The representatively shown configuration includes an extension member positioned and attached at each aperture. In particular aspects, the length 129 of each extension member can be adjusted so that the final outlet openings 118*c* of the extension members are positioned to better follow the contour of the forming surface that is cooperating with the curved nozzle. For example, the extension member lengths and alignments can be configured to provide desired discharge angles (e.g. angles 44 and 52) and discharge heights (e.g. height distances 46 and 54) relative the cooperating forming surface. As a result, the more effective following of the forming surface contour can help to provide the desired concentrations of particulate material into the desired locations along the thickness and cross-directional width dimensions of their corresponding strata within the formed web 94.

With reference to FIGS. 19 and 19A, the operation and effectiveness of the curved nozzle 86 can be further modified by joining together two or more differently configured conduit or pipe sections. For example, the curved nozzle may include a first conduit section 124 joined to a second conduit section 126. The first conduit section can have a relatively smaller radius of curvature 110, and the second conduit section can have a relatively larger radius of curvature. The distribution, outlet apertures are formed through the radially outward wall of at least the second conduit section, and the first conduit section may or may not include outlet apertures. The smaller bend radius of the first conduit section 124 can more effectively position more of the moving particulate material toward the wall surface along the outward-side of the bend curvature of the first conduit section prior to moving the particulate material into the second conduit section. The larger bend radius of the second conduit section 126 can allow an improved control over the placement of particulate material onto selected locations along the length of the forming path. Additionally, the larger bend radius can better avoid excessive changes in the distance between the nozzle outlet apertures and the forming surface 22.

Figures 18, 18A:
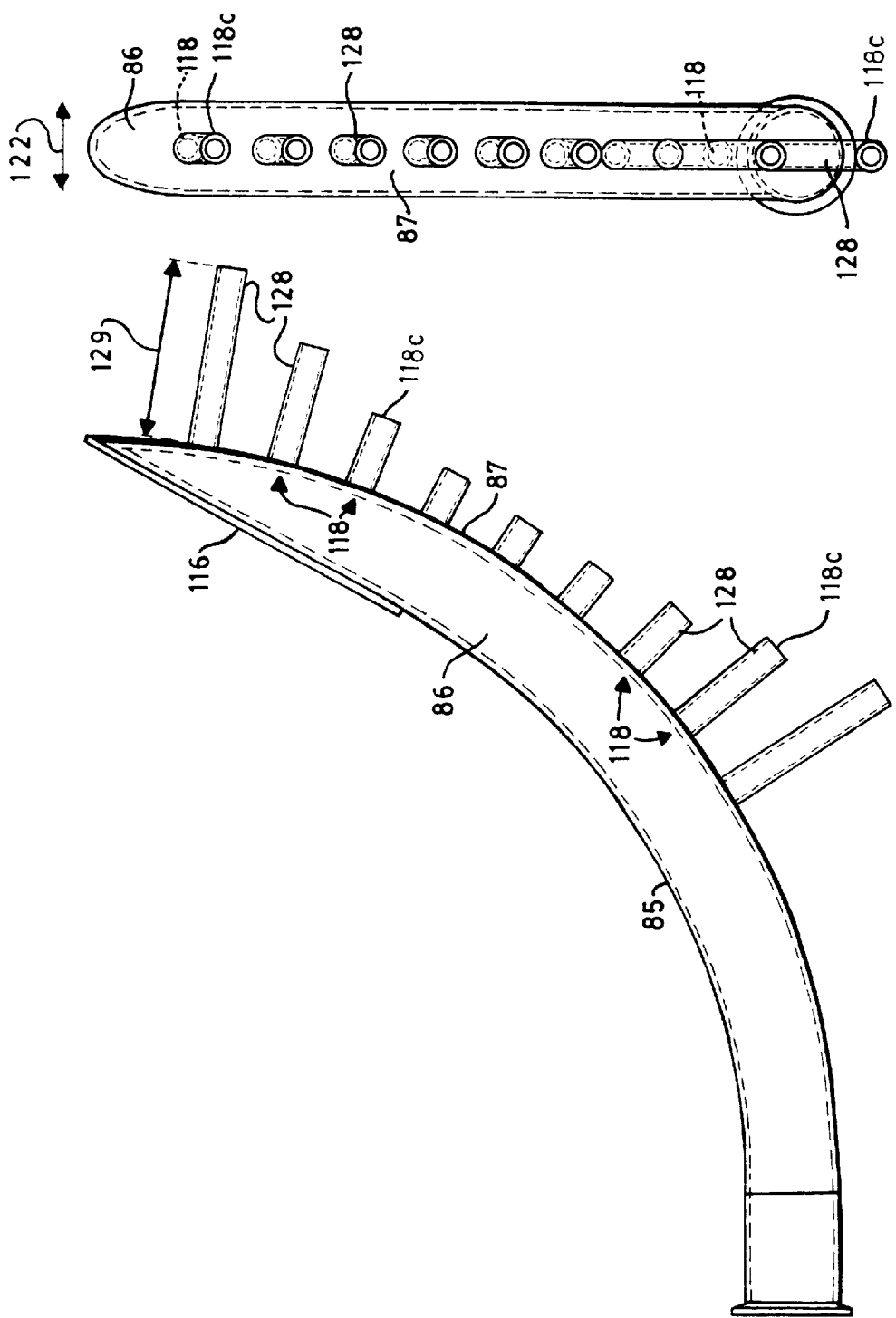
FIG. 18 representatively shows a schematic side view of a curved nozzle which includes a system of extension members located at the nozzle apertures.
FIG. 18A representatively shows a schematic end view of the curved nozzle of FIG. 18.

In the representatively shown configuration, the nozzle can be a conduit or pipe with a generally circular cross-section. A representative construction of the nozzle pipe may, for example, have a substantially circular diameter 114 (e.g. FIG. 13) of approximately 5.7 cm (about 2.25 inch) and can have a radius of curvature 110 of about 25.4 cm (about 10 inch). Approximately thirteen, substantially circular holes can be generally evenly spaced and generally aligned along the length of the radially outboard wall of the curved nozzle, and each hole can have a diameter of about 0.8 cm (about 5/16 inch). The end of the nozzle can be terminated with an end angle that is oriented approximately 45 degrees relative to the radial direction along the local radius of curvature of the curved nozzle. Additionally, the terminal end of the nozzle may be capped with a plate member.

Where the curved nozzle 86 has an array of outlet apertures, a designated nozzle angle with respect to the machine-direction 120 can, for the purposes of the present disclosure, be determined by employing the following procedure. A first outlet line 130 is projected through the center of the first aperture outlet 118a (located farthest from the distal end of the curved nozzle), and the first outlet line is aligned parallel to a facing direction of the first outlet, as representatively shown in FIG. 20. Where the first outlet is a simple opening through the radially outboard wall 87, its outlet facing direction is taken as being perpendicular to the outboard wall at the location of the first outlet. Where the first outlet includes additional structure, such as a first extension conduit member 128 (e.g. FIG. 18), the facing direction of the first outlet is the direction of movement imparted at the exit of the associated, corresponding extension member.

Additionally, another, "last" outlet line 132 is projected through the center of the last aperture outlet 118b (located closest to the distal end of the curved nozzle). The last outlet line is aligned parallel to a facing direction of the last outlet, as representatively shown in FIG. 20. Where the last outlet is a simple opening through the radially outboard wall 87, its outlet facing direction is taken as being perpendicular to the outboard wall at the location of the last outlet. Where the last outlet includes additional structure, such as a last extension conduit member 128 (e.g. FIG. 18), the facing direction of the last outlet is the direction of movement imparted at the exit of the associated, corresponding extension member.

Figure 20:
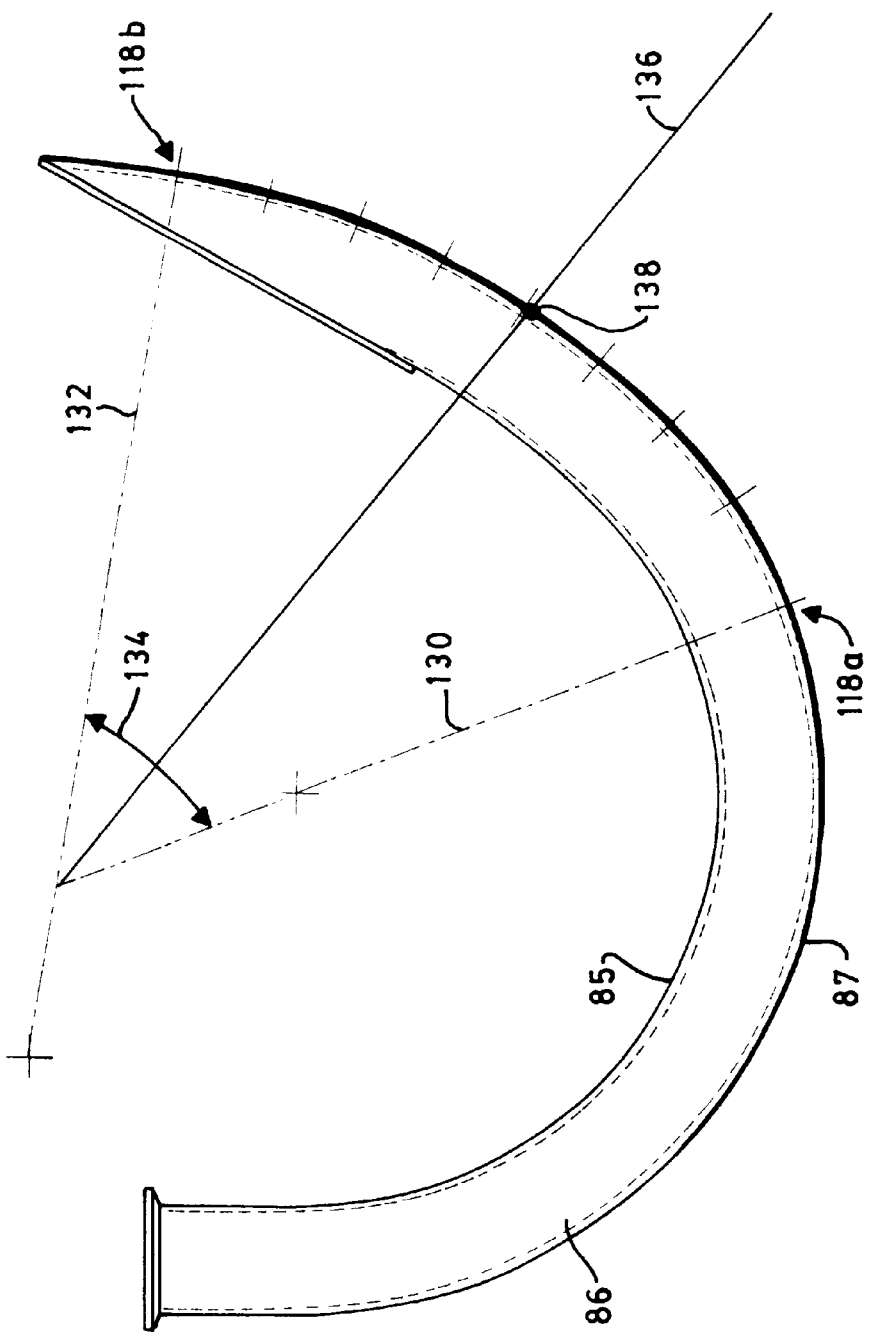
FIG. 20 representatively shows a schematic side view of a curved nozzle along with a nozzle reference line and a nozzle reference point employed to determine a corresponding nozzle tilt angle and a corresponding path-position value.

In the side view representatively shown in FIG. 20, the curved nozzle lies substantially parallel to its plane of curvature, and the viewed projections of the first and last outlet lines intersect to form a base angle 134. An intermediate, reference line 136 is aligned to bisect the base angle, and is projected to intersect the outside surface of the radially the radially outward wall 87 at a designated nozzle reference point 138. The nozzle reference line 136 can then be employed to determine a designated nozzle tilt angle of the curved nozzle, and the nozzle reference point 138 can be employed to determine a designated path-position value of the curved nozzle.

For the purposes of the present disclosure, the designated tilt angle of the curved nozzle can be determined by projecting a local line that intersects the reference point 138 and is perpendicular to a corresponding local section of the forming surface 22 which is positioned directly under the reference point 138. The designated nozzle angle (e.g. 44, 52) is the machine-direction-component of the angle formed between the nozzle reference line 136 and the local perpendicular line to the forming surface that passes through the nozzle reference point 138.

The designated path-position value of the curved nozzle is, for the purposes of the present disclosure, determined by measuring a path-location at the nozzle reference point 138. An assigned path-location of the curved nozzle can be determined by employing the previously described local line that intersects the reference point and is perpendicular to a corresponding local section of the forming surface which is positioned directly under the reference point 138. The assigned location of the curved nozzle is the path length distance between the chamber entrance 98, and the intersection of this local perpendicular line with the forming surface. The assigned location of the curved nozzle can then be employed to calculate a corresponding, designated path-position percentage value for the curved nozzle.

Having described the invention in rather full detail, it will be readily apparent that various changes and modifications can be made without departing from the spirit of the invention. All of such changes and modifications are contemplated as being within the scope of the invention as defined by the subjoined claims.

We claim:

1. An apparatus for depositing particulate material in an airlaid fibrous web, the apparatus comprising:
   a forming chamber;
   a forming surface which can be moved through said forming chamber, said forming surface configured to accumulate fibrous material thereon as the forming surface is moved through said forming chamber;
   a fiber source which can provide said fibrous material into said forming chamber for laying onto said forming surface to form said fibrous web;
   an arcuate curved nozzle which is positioned within said forming chamber at a location spaced from said forming surface, said curved nozzle having a radius of curvature of at least a minimum of about 2.54 cm and a curved arc length of at least a minimum of about 3 cm, and said curved nozzle configured to include a plurality of outlet apertures in an array located in a radially outboard wall of said curved nozzle to deliver said particulate material into said forming chamber.

2. An apparatus as recited in claim 1, wherein said outlet apertures are generally aligned along a longitudinal dimension of said curved nozzle.

3. An apparatus as recited in claim 1, wherein said outlet apertures have different sizes.

4. An apparatus as recited in claim 1, wherein said outlet apertures gradually increase in size along a longitudinal dimension of said curved nozzle.

5. An apparatus as recited in claim 1, wherein said array of outlet apertures includes substantially circular holes.

6. An apparatus as recited in claim 1, wherein said array of outlet apertures includes slots.

7. An apparatus as recited in claim 1, wherein said curved nozzle is configured to deliver said particulate material in a desired distribution and concentration into the fibrous material which accumulates on said forming surface.

8. An apparatus as recited in claim 1, wherein said apparatus provides a forming path length; and said curved nozzle is located within a first 25% of said forming path length.

9. An apparatus as recited in claim 1, wherein said apparatus provides a forming path length; and said curved nozzle is located within a second 25% of said forming path length.

10. An apparatus as recited in claim 1, wherein a longitudinal dimension of said curved nozzle is generally aligned along a movement direction of said forming surface.

11. An apparatus as recited in claim 1, wherein said curved nozzle includes a radius of curvature of not more than about 305 cm.

12. An apparatus as recited in claim 1, wherein curved nozzle includes a non-uniform radius of curvature along said curved arc length of said curved nozzle.

13. An apparatus as recited in claim 12, wherein curved nozzle has a first conduit section with a first radius of curvature, and a second conduit section with a second radius of curvature which is greater than said first radius of curvature.

14. A method for depositing particulate material in an airlaid fibrous web, comprising a positioning of an arcuate curved nozzle within a forming chamber at a location spaced from a movable forming surface to deliver said particulate material onto fibrous material which has accumulated on said forming surface; providing said curved nozzle with a radius of curvature of at least a minimum of about 2.54 cm and a curved arc length of at least a minimum of about 3 cm; and configuring said curved nozzle to include a plurality of outlet apertures in an array located in a radially outboard wall of said curved nozzle.

15. A method as recited in claim 14, further including an aligning of said curved nozzle generally along a longitudinal dimension of the method.

16. A method as recited in claim 14, further including a configuring of said outlet apertures with different sizes.

17. A method as recited in claim 14, further including a configuring of said outlet apertures with gradually increasing size along a longitudinal dimension of said curved nozzle.

18. A method as recited in claim 14, further including a configuring of said outlet apertures to include substantially circular holes.

19. A method as recited in claim 14, further including a configuring of said outlet apertures to include slots.

20. A method as recited in claim 14, further including a configuring of said curved nozzle to have a radius of curvature of not more than about 305 cm.

21. A method as recited in claim 14, further including a configuring of said curved nozzle to have a non-uniform radius of curvature along said curved arc length of said curved nozzle.

22. A method as recited in claim 21, further including a configuring of said curved nozzle to have a first conduit section with a first radius of curvature, and a second conduit section with a second radius of curvature which is greater than said first radius of curvature.

23. A method for depositing particulate material in an airlaid fibrous web, the method comprising:

a moving of a forming surface through a forming chamber;

a laying of said fibrous material onto said forming surface to form said fibrous web;

a delivering of said particulate material into said forming chamber with an arcuate curved nozzle which is positioned within said forming chamber at a location spaced from said forming surface, said curved nozzle having been provided with a radius of curvature of at least a minimum of about 2.54 cm and a curved arc length of at least a minimum of about 3 cm, and said curved nozzle having been configured to include a plurality of outlet apertures located in a radially outboard wall of said curved nozzle.

24. A method as recited in claim 23, further comprising:

a configuring of said forming surface to accumulate fibrous material thereon as the forming surface moves through said forming chamber.

25. A method for depositing particulate material in an airlaid fibrous web, includes a providing of a forming chamber;

a providing of a forming surface which can be moved through said forming chamber, said forming surface configured to accumulate fibrous material thereon as said forming surface is moved through said forming chamber;

a providing of a fiber source which can provide said fibrous material into said forming chamber for laying onto said forming surface to form said fibrous web;

a positioning of an arcuate curved nozzle within said forming chamber at a location spaced from said forming surface, said curved nozzle having been provided with a radius of curvature of at least about 2.54 cm and a curved arc length of at least a minimum of about 3 cm, and said curved nozzle having been configured to include a plurality of outlet apertures located in a radially outboard wall of said curved nozzle to deliver said particulate material onto said fibrous material which accumulates on said forming surface.

\* \* \* \* \*

UNITED STATES PATENT AND TRADEMARK OFFICE
CERTIFICATE OF CORRECTION

PATENT NO.   : 6,202,259 B1
DATED        : March 20, 2001
INVENTOR(S)  : Randy Keith Burr et al.

It is certified that error appears in the above-identified patent and that said Letters Patent is hereby corrected as shown below:

Column 11,
Line 44, delete "provided", and substitute -- provide --.

Column 14,
Line 32, delete " "s" ", and substitute -- "minus" --.
Line 39, delete "-480," and substitute -- -48° --.

Column 16,
Line 3, delete "8°", and substitute -- -48° --.

Signed and Sealed this

First Day of January, 2002

Attest:

Attesting Officer

JAMES E. ROGAN
Director of the United States Patent and Trademark Office